United States Patent
Suzuki et al.

(10) Patent No.: US 9,156,900 B2
(45) Date of Patent: Oct. 13, 2015

(54) CONTROL AGENT FOR CONTROLLING UNDIFFERENTIATED STATE AND USE THEREOF

(75) Inventors: Harukazu Suzuki, Yokohama (JP); Yuki Hasegawa, Yokohama (JP); Alistair Forrest, Yokohama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/006,495

(22) PCT Filed: Mar. 30, 2012

(86) PCT No.: PCT/JP2012/058665
§ 371 (c)(1),
(2), (4) Date: Sep. 20, 2013

(87) PCT Pub. No.: WO2012/133811
PCT Pub. Date: Oct. 4, 2012

(65) Prior Publication Data
US 2014/0017790 A1  Jan. 16, 2014

(30) Foreign Application Priority Data
Mar. 31, 2011  (JP) ................. 2011-077473

(51) Int. Cl.
| | |
|---|---|
| C12N 5/10 | (2006.01) |
| C12N 1/00 | (2006.01) |
| C12N 5/073 | (2010.01) |
| C12N 15/09 | (2006.01) |
| C07K 14/52 | (2006.01) |
| C12N 5/074 | (2010.01) |

(52) U.S. Cl.
CPC ............ C07K 14/523 (2013.01); C07K 14/521 (2013.01); C12N 5/0696 (2013.01); *C12N 2501/20* (2013.01); *C12N 2501/235* (2013.01); *C12N 2501/998* (2013.01); *C12N 2510/00* (2013.01)

(58) Field of Classification Search
USPC ......................................... 435/377
See application file for complete search history.

(56) References Cited

U.S. PATENT DOCUMENTS

| | | | | |
|---|---|---|---|---|
| 5,714,578 | A * | 2/1998 | Yoshimura et al. ............ 530/324 |
| 6,100,389 | A | 8/2000 | Li et al. | |
| 6,800,480 | B1 | 10/2004 | Bodnar et al. | |
| 2003/0175956 | A1 | 9/2003 | Bodnar et al. | |
| 2004/0185450 | A1 | 9/2004 | Heavner et al. | |
| 2010/0075416 | A1 * | 3/2010 | Primiano ........................ 435/366 |

FOREIGN PATENT DOCUMENTS

| | | |
|---|---|---|
| JP | 2001-017163 | 1/2001 |
| JP | 2006-204292 | 8/2006 |
| JP | 2006-345702 | 12/2006 |
| JP | 2009-072186 | 4/2009 |
| JP | 2010-004796 | 1/2010 |
| WO | 99/20740 | 4/1999 |
| WO | 00/78334 | 12/2000 |
| WO | 2010/033138 | 3/2010 |

OTHER PUBLICATIONS

Alberti et al., "Functional immobilization of signaling proteins enables control of stem cell fate," Nat. Meth. 5:645-650 (2008).*
Chambers, et al., "Functional Expression Cloning of Nanog, a Pluripotency Sustaining Factor in Embryonic Stem Cells," Cell 113:643-655 (2003).- included in IDS of Sep. 20, 2013.*
Chin et al., "Identification of proteins from feeder conditioned medium that support human embryonic stem cells," J. Biotech. 130:320-328 (2007).*
Thomson et al., "Isolation of a Primate Embryonic Stem Cell Line", Proc. Natl. Acad. Sci. USA, vol. 92, pp. 7844-7848, Aug. 1995.
Thomson et al., "Embryonic Stem Cell Lines Derived from Human Blastocysts", Science, vol. 282, pp. 1145-1147, Nov. 1998.
Reubinoff et al., "Embryonic Stem Cell Lines from Human Blastocysts: Somatic Differentiation in Vitro", Nat. Biotechnol., vol. 18, pp. 399-404, Apr. 2000.
Xu et al., "Feeder-Free Growth of Undifferentiated Human Embryonic Stem Cells", Nat. Biotechnol., vol. 19, pp. 971-974, Oct. 2001.
Amit et al., "Feeder Layer- and Serum-Free Culture of Human Embryonic Stem Cells", Biol. Reprod., vol. 70, pp. 837-845, 2004.
Chambers et al., "Functional Expression Cloning of Nanog, a Pluripotency Sustaining Factor in Embryonic Stem Cells", Cell, vol. 113, pp. 643-655, May 2003.
Mitsui et al., "The Homeoprotein Nanog Is Required for Maintenance of Pluripotency in Mouse Epiblast and ES Cells", Cell, vol. 113, pp. 631-642, May 2003.
Ying et al., "BMP Induction of Id Proteins Suppresses Differentiation and Sustains Embryonic Stem Cell Self-Renewal in Collaboration withSTAT3", Cell, vol. 115, pp. 281-292, Oct. 2003.
Mitalipova et al., "Human Embryonic Stem Cell Lines Derived from Discarded Embryos", Stem Cells, vol. 21, pp. 521-526, 2003.

(Continued)

*Primary Examiner* — Julie Ha
*Assistant Examiner* — Kristina M Hellman
(74) *Attorney, Agent, or Firm* — Hamre, Schumann, Mueller & Larson, P.C.

(57) ABSTRACT

The present invention aims to provide a novel undifferentiated state-control agent that maintains and/or improves an undifferentiated state of undifferentiated cells. CCL2 or a protein containing a functional domain thereof is used as the undifferentiated state-control agent. By culturing undifferentiated cells in the presence of the control agent, it is possible to maintain and/or improve an undifferentiated state of the undifferentiated cells. Examples of the undifferentiated cells include embryonic stem cells (ES cells) and induced pluripotent stem cells (iPS cells). The origin of the cells is not particularly limited, and may be a human, mouse, or the like, for example.

5 Claims, 11 Drawing Sheets

(56) References Cited

OTHER PUBLICATIONS

Heins et al., "Derivation, Characterization, and Differentiation of Human Embryonic Stem Cells", Stem Cells, vol. 22, pp. 367-376, 2004.

Sato et al., "Maintenance of Pluripotency in Human and Mouse Embryonic Stem Cells through Activation of Wnt Signaling by a PharmacologicalGSK-3-Specific Inhibitor", Nature Medicine, vol. 10, pp. 55-63, 2004.

Beattie et al., "Activin A Maintains Pluripotency of Human Embryonic Stem Cells in the Absence of Feeder Layers", Stem Cells, vol. 23, pp. 489-495, 2005.

Boiani et al., "Regulatory Networks in Embryo-Derived Pluripotent Stem Cells", Nature Reviews Molecular Cell Biology, vol. 6, pp. 872-884, Nov. 2005.

Totonchi et al., "Feeder- and Serum-free Establishment and Expansion of Human Induced Pluripotent Stem Cells", Int. J. Dev. Biol., vol. 54, pp. 877-886, 2010.

Hasegawa et al., "CC Chemokine Ligand 2 and Leukemia Inhibitory Factor Cooperatively Promote Pluripotency in Mouse Induced Pluripotent Cells", Stem Cells, vol. 29, pp. 1196-1205, 2011.

Hasegawa et al., "CC Chemokine Ligand 2 and LIF Cooperatively Promote Pluripotency in Mouse Induced Pluripotent Cells", Program of the34th MBSJ (The Molecular Biology Society of Japan) Annual Meeting, 1P-0176, 2011.

Ohnishi et al., "Effect of Hypoxia on Gene Expression of Bone Marrow-Derived Mesenchymal Stem Cells and Mononuclear Cells", Stem Cells, vol. 25, pp. 1166-1177, 2007.

Hennrick et al., "Lung Cells from Neonates Show a Mesenchymal Stem Cell Phenotype", American Journal of Respiratory and Critical Care Medicine, vol. 175, pp. 1158-1164, 2007.

\* cited by examiner

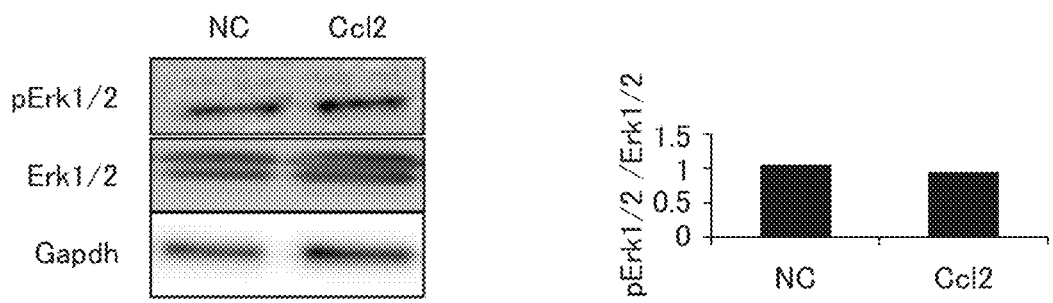
FIG. 7A
FIG. 7B
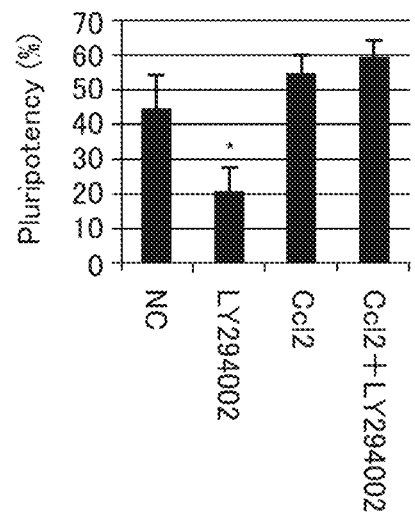
FIG. 8
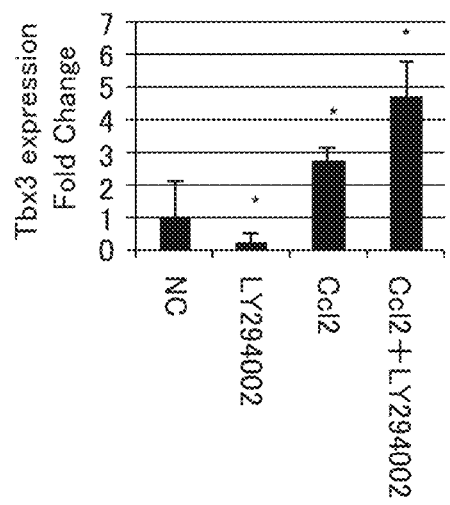
FIG. 9

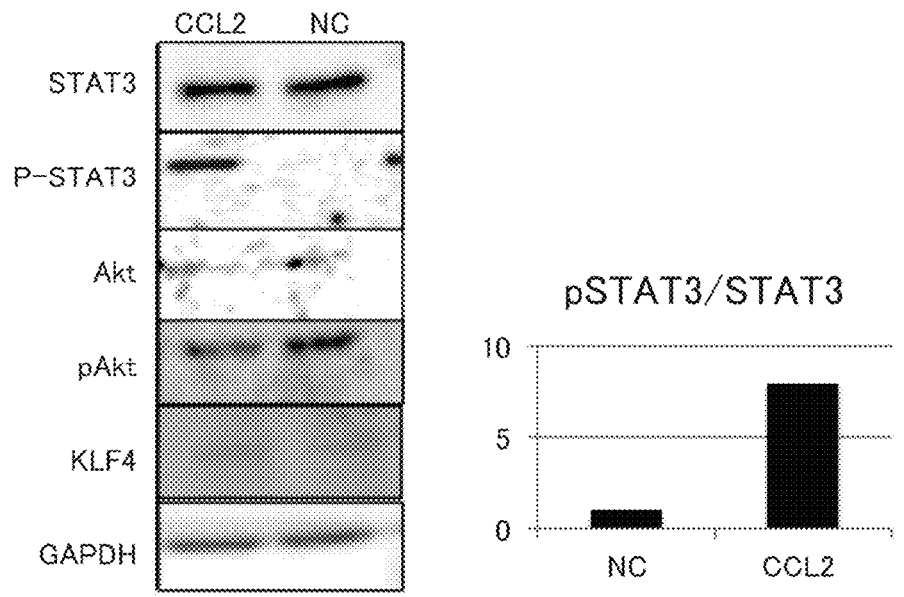
FIG. 15A
FIG. 15B
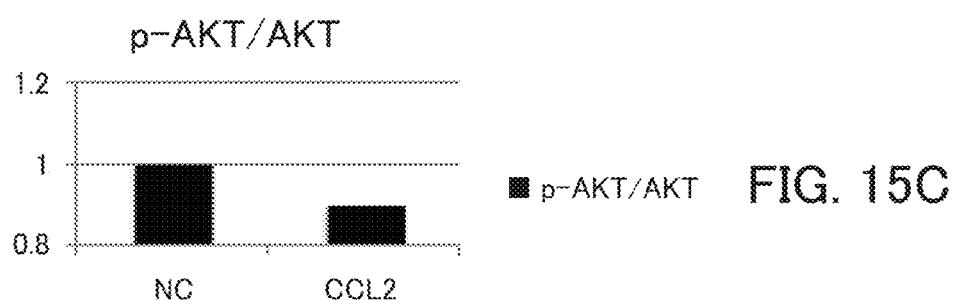
FIG. 15C
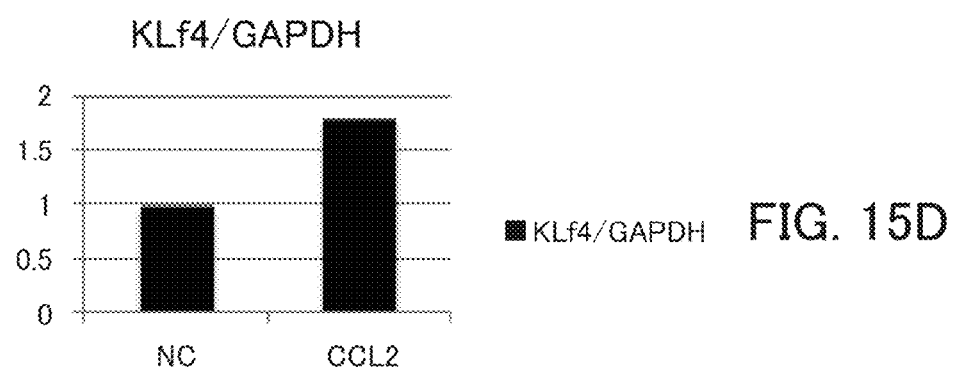
FIG. 15D

CCL2 (−)/bFGF (+)

CCL2 (+)/LIF (+)

CCL2 (+) /LIF (−) /bFGF (−)

CCL2 (+) /LIF (+) /bFGF (−)

SEQUENCE LISTING

```
<160> NUMBER OF SEQ ID NOS: 94

<210> SEQ ID NO 1
<211> LENGTH: 99
<212> TYPE: PRT
<213> ORGANISM: Homo sapiens

<400> SEQUENCE: 1

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
                20                  25                  30

Thr Cys Cys Tyr Asn Phe Thr Asn Arg Lys Ile Ser Val Gln Arg Leu
            35                  40                  45

Ala Ser Tyr Arg Arg Ile Thr Ser Ser Lys Cys Pro Lys Glu Ala Val
        50                  55                  60

Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr

<210> SEQ ID NO 2
<211> LENGTH: 76
<212> TYPE: PRT
<213> ORGANISM: Homo sapiens

<400> SEQUENCE: 2

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
        50                  55                  60

Asp His Leu Asp Lys Gln Thr Gln Thr Pro Lys Thr
65                  70                  75

<210> SEQ ID NO 3
<211> LENGTH: 148
<212> TYPE: PRT
<213> ORGANISM: Mus musculus

<400> SEQUENCE: 3
```

```
Met Gln Val Pro Val Met Leu Leu Gly Leu Leu Phe Thr Val Ala Gly
1               5                   10                  15

Trp Ser Ile His Val Leu Ala Gln Pro Asp Ala Val Asn Ala Pro Leu
            20                  25                  30

Thr Cys Cys Tyr Ser Phe Thr Ser Lys Met Ile Pro Met Ser Arg Leu
        35                  40                  45

Glu Ser Tyr Lys Arg Ile Thr Ser Ser Arg Cys Pro Lys Glu Ala Val
    50                  55                  60

Val Phe Val Thr Lys Leu Lys Arg Glu Val Cys Ala Asp Pro Lys Lys
65                  70                  75                  80

Glu Trp Val Gln Thr Tyr Ile Lys Asn Leu Asp Arg Asn Gln Met Arg
                85                  90                  95

Ser Glu Pro Thr Thr Leu Phe Lys Thr Ala Ser Ala Leu Arg Ser Ser
            100                 105                 110

Ala Pro Leu Asn Val Lys Leu Thr Arg Lys Ser Glu Ala Asn Ala Ser
        115                 120                 125

Thr Thr Phe Ser Thr Thr Thr Ser Ser Thr Ser Val Gly Val Thr Ser
    130                 135                 140

Val Thr Val Asn
145
```

<210> SEQ ID NO 4
<211> LENGTH: 125
<212> TYPE: PRT
<213> ORGANISM: Mus musculus

<400> SEQUENCE: 4

```
Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60

Lys Asn Leu Asp Arg Asn Gln Met Arg Ser Glu Pro Thr Thr Leu Phe
65                  70                  75                  80

Lys Thr Ala Ser Ala Leu Arg Ser Ser Ala Pro Leu Asn Val Lys Leu
                85                  90                  95

Thr Arg Lys Ser Glu Ala Asn Ala Ser Thr Thr Phe Ser Thr Thr Thr
            100                 105                 110

Ser Ser Thr Ser Val Gly Val Thr Ser Val Thr Val Asn
        115                 120                 125
```

<210> SEQ ID NO 5
<211> LENGTH: 300
<212> TYPE: DNA
<213> ORGANISM: Homo sapiens

<400> SEQUENCE: 5

```
atgaaagtct ctgccgccct tctgtgcctg ctgctcatag cagccacctt cattccccaa    60
gggctcgctc agccagatgc aatcaatgcc ccagtcacct gctgttataa cttcaccaat    120
aggaagatct cagtgcagag gctcgcgagc tatagaagaa tcaccagcag caagtgtccc    180
aaagaagctg tgatcttcaa gaccattgtg gccaaggaga tctgtgctga ccccaagcag    240
aagtgggttc aggattccat ggaccacctg acaagcaaa cccaaactcc gaagacttga    300
```

<210> SEQ ID NO 6
<211> LENGTH: 447
<212> TYPE: DNA
<213> ORGANISM: Mus musculus

<400> SEQUENCE: 6

```
atgcaggtcc ctgtcatgct tctgggcctg ctgttcacag ttgccggctg gagcatccac      60
gtgttggctc agccagatgc agttaacgcc ccactcacct gctgctactc attcaccagc     120
aagatgatcc caatgagtag gctggagagc tacaagagga tcaccagcag caggtgtccc     180
aaagaagctg tagtttttgt caccaagctc aagagagagg tctgtgctga ccccaagaag     240
gaatgggtcc agacatacat taaaaacctg gatcggaacc aaatgagatc agaacctaca     300
actttattta aaactgcatc tgccctaagg tcttcagcac ctttgaatgt gaagttgacc     360
cgtaaatctg aagctaatgc atccactacc ttttccacaa ccacctcaag cacttctgta     420
ggagtgacca gtgtgacagt gaactag                                         447
```

<210> SEQ ID NO 7
<211> LENGTH: 25
<212> TYPE: RNA
<213> ORGANISM: Artificial
<220> FEATURE:
<223> OTHER INFORMATION: siRNA

<400> SEQUENCE: 7

```
cauucaccag caagaugauc ccaau                                            25
```

<210> SEQ ID NO 8
<211> LENGTH: 25
<212> TYPE: RNA
<213> ORGANISM: Artificial
<220> FEATURE:
<223> OTHER INFORMATION: siRNA

<400> SEQUENCE: 8

```
caaguuugug cugaaggcgu cucug                                            25
```

<210> SEQ ID NO 9
<211> LENGTH: 20
<212> TYPE: DNA
<213> ORGANISM: Artificial
<220> FEATURE:
<223> OTHER INFORMATION: primer

<400> SEQUENCE: 9

```
gaagcccatc accatcttcc                                                  20
```

<210> SEQ ID NO 10
<211> LENGTH: 20
<212> TYPE: DNA
<213> ORGANISM: Artificial
<220> FEATURE:
<223> OTHER INFORMATION: primer

<400> SEQUENCE: 10

```
gatgaccctt ttggctccac                                                  20
```

<210> SEQ ID NO 11
<211> LENGTH: 22
<212> TYPE: DNA
<213> ORGANISM: Artificial
<220> FEATURE:

```
<223> OTHER INFORMATION: primer

<400> SEQUENCE: 11
tagtgctgca tgaggagaca cc                                              22

<210> SEQ ID NO 12
<211> LENGTH: 22
<212> TYPE: DNA
<213> ORGANISM: Artificial
<220> FEATURE:
<223> OTHER INFORMATION: primer

<400> SEQUENCE: 12
tttgcctctt ctccacagac ac                                              22

<210> SEQ ID NO 13
<211> LENGTH: 21
<212> TYPE: DNA
<213> ORGANISM: Artificial
<220> FEATURE:
<223> OTHER INFORMATION: primer

<400> SEQUENCE: 13
tatctgaaag ggaccgtgct c                                               21

<210> SEQ ID NO 14
<211> LENGTH: 21
<212> TYPE: DNA
<213> ORGANISM: Artificial
<220> FEATURE:
<223> OTHER INFORMATION: primer

<400> SEQUENCE: 14
atccggatgt gctcagtaag g                                               21

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
ctttcctgcc agaccagatg                                                 20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
ttcttcccct ctttggcttg                                                 20

<210> SEQ ID NO 17
<211> LENGTH: 19
<212> TYPE: DNA
<213> ORGANISM: Artificial
<220> FEATURE:
<223> OTHER INFORMATION: primer

<400> SEQUENCE: 17
aagtactcag cctccagca                                                  19
```

```
<210> SEQ ID NO 18
<211> LENGTH: 20
<212> TYPE: DNA
<213> ORGANISM: Artificial
<220> FEATURE:
<223> OTHER INFORMATION: primer

<400> SEQUENCE: 18
gtgctgagcc cttctgaatc                                               20

<210> SEQ ID NO 19
<211> LENGTH: 20
<212> TYPE: DNA
<213> ORGANISM: Artificial
<220> FEATURE:
<223> OTHER INFORMATION: primer

<400> SEQUENCE: 19
agtttgccaa gctgctgaag                                               20

<210> SEQ ID NO 20
<211> LENGTH: 21
<212> TYPE: DNA
<213> ORGANISM: Artificial
<220> FEATURE:
<223> OTHER INFORMATION: primer

<400> SEQUENCE: 20
tcttaaggct gagctgcaag g                                             21

<210> SEQ ID NO 21
<211> LENGTH: 20
<212> TYPE: DNA
<213> ORGANISM: Artificial
<220> FEATURE:
<223> OTHER INFORMATION: primer

<400> SEQUENCE: 21
tgaacgcctt catggtatgg                                               20

<210> SEQ ID NO 22
<211> LENGTH: 20
<212> TYPE: DNA
<213> ORGANISM: Artificial
<220> FEATURE:
<223> OTHER INFORMATION: primer

<400> SEQUENCE: 22
ttgtgcatct tggggttctc                                               20

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
agtcgttgaa taccgcgttg                                               20

<210> SEQ ID NO 24
<211> LENGTH: 20
<212> TYPE: DNA
<213> ORGANISM: Artificial
<220> FEATURE:
<223> OTHER INFORMATION: primer
```

```
<400> SEQUENCE: 24
agaaacggtt tggtcgaagg                                              20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
cagctcacac tgcagtccat                                              20

<210> SEQ ID NO 26
<211> LENGTH: 20
<212> TYPE: DNA
<213> ORGANISM: Artificial
<220> FEATURE:
<223> OTHER INFORMATION: primer

<400> SEQUENCE: 26
tggagacagc aggagaggat                                              20

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
gctgggattc acctcaagaa                                              20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
aagggagctt cagggtcaag                                              20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
tctccaggaa cttcgtgtcc                                              20

<210> SEQ ID NO 30
<211> LENGTH: 20
<212> TYPE: DNA
<213> ORGANISM: Artificial
<220> FEATURE:
<223> OTHER INFORMATION: primer

<400> SEQUENCE: 30
ctccgttttc aatcccagag                                              20

<210> SEQ ID NO 31
<211> LENGTH: 20
```

```
<212> TYPE: DNA
<213> ORGANISM: Artificial
<220> FEATURE:
<223> OTHER INFORMATION: primer

<400> SEQUENCE: 31
cccaatgagt aggctggaga                                               20

<210> SEQ ID NO 32
<211> LENGTH: 20
<212> TYPE: DNA
<213> ORGANISM: Artificial
<220> FEATURE:
<223> OTHER INFORMATION: primer

<400> SEQUENCE: 32
tctggaccca ttccttcttg                                               20

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
gcacaggtac cacccctaga                                               20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
gccccaaagt agcctttctc                                               20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gtaaggtccc gcctttaagc                                               20

<210> SEQ ID NO 36
<211> LENGTH: 20
<212> TYPE: DNA
<213> ORGANISM: Artificial
<220> FEATURE:
<223> OTHER INFORMATION: primer

<400> SEQUENCE: 36
cgccgaagaa ggtagtgttc                                               20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
```
gccctgatgt ttcccatcta                                              20

<210> SEQ ID NO 38
<211> LENGTH: 20
<212> TYPE: DNA
<213> ORGANISM: Artificial
<220> FEATURE:
<223> OTHER INFORMATION: primer

<400> SEQUENCE: 38
ttttgggatg cttagggttg                                              20

<210> SEQ ID NO 39
<211> LENGTH: 20
<212> TYPE: DNA
<213> ORGANISM: Artificial
<220> FEATURE:
<223> OTHER INFORMATION: primer

<400> SEQUENCE: 39
acccaggtct caggttcaga                                              20

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
tgctgttgct gttcctgttc                                              20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
ctgcttccag gacacattgc                                              20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tgtgggcact tgtgacactt                                              20

<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
ggaagtttcc tgtgtgtctg c                                            21

<210> SEQ ID NO 44
<211> LENGTH: 20
<212> TYPE: DNA
<213> ORGANISM: Artificial

```
<220> FEATURE:
<223> OTHER INFORMATION: primer

<400> SEQUENCE: 44
cggccatccc tacacatatc                                                    20

<210> SEQ ID NO 45
<211> LENGTH: 20
<212> TYPE: DNA
<213> ORGANISM: Artificial
<220> FEATURE:
<223> OTHER INFORMATION: primer

<400> SEQUENCE: 45
catgcactgc caagtttcag                                                    20

<210> SEQ ID NO 46
<211> LENGTH: 20
<212> TYPE: DNA
<213> ORGANISM: Artificial
<220> FEATURE:
<223> OTHER INFORMATION: primer

<400> SEQUENCE: 46
ccacaccgtt caccaaagta                                                    20

<210> SEQ ID NO 47
<211> LENGTH: 20
<212> TYPE: DNA
<213> ORGANISM: Artificial
<220> FEATURE:
<223> OTHER INFORMATION: primer

<400> SEQUENCE: 47
ggagactccg agttgaccac                                                    20

<210> SEQ ID NO 48
<211> LENGTH: 20
<212> TYPE: DNA
<213> ORGANISM: Artificial
<220> FEATURE:
<223> OTHER INFORMATION: primer

<400> SEQUENCE: 48
ggccagtctt cctcgtacac                                                    20

<210> SEQ ID NO 49
<211> LENGTH: 20
<212> TYPE: DNA
<213> ORGANISM: Artificial
<220> FEATURE:
<223> OTHER INFORMATION: primer

<400> SEQUENCE: 49
cagtctgaag gcacagcaag                                                    20

<210> SEQ ID NO 50
<211> LENGTH: 20
<212> TYPE: DNA
<213> ORGANISM: Artificial
<220> FEATURE:
<223> OTHER INFORMATION: primer

<400> SEQUENCE: 50
ccactggtgg gaaaataacc                                                    20
```

```
<210> SEQ ID NO 51
<211> LENGTH: 20
<212> TYPE: DNA
<213> ORGANISM: Artificial
<220> FEATURE:
<223> OTHER INFORMATION: primer

<400> SEQUENCE: 51
tgtccctggg aagctgttat                                              20

<210> SEQ ID NO 52
<211> LENGTH: 20
<212> TYPE: DNA
<213> ORGANISM: Artificial
<220> FEATURE:
<223> OTHER INFORMATION: primer

<400> SEQUENCE: 52
ctttggagtt ggggttttca                                              20

<210> SEQ ID NO 53
<211> LENGTH: 20
<212> TYPE: DNA
<213> ORGANISM: Artificial
<220> FEATURE:
<223> OTHER INFORMATION: primer

<400> SEQUENCE: 53
gcctgctgtc cttcagaaac                                              20

<210> SEQ ID NO 54
<211> LENGTH: 20
<212> TYPE: DNA
<213> ORGANISM: Artificial
<220> FEATURE:
<223> OTHER INFORMATION: primer

<400> SEQUENCE: 54
caaactgcct taggccaatc                                              20

<210> SEQ ID NO 55
<211> LENGTH: 20
<212> TYPE: DNA
<213> ORGANISM: Artificial
<220> FEATURE:
<223> OTHER INFORMATION: primer

<400> SEQUENCE: 55
agcacaatgt gagcatggac                                              20

<210> SEQ ID NO 56
<211> LENGTH: 20
<212> TYPE: DNA
<213> ORGANISM: Artificial
<220> FEATURE:
<223> OTHER INFORMATION: primer

<400> SEQUENCE: 56
acggacaggg cttttatcct                                              20

<210> SEQ ID NO 57
<211> LENGTH: 20
<212> TYPE: DNA
<213> ORGANISM: Artificial
<220> FEATURE:
<223> OTHER INFORMATION: primer
```

```
<400> SEQUENCE: 57
gatggctcag gcaagaagac                                                20

<210> SEQ ID NO 58
<211> LENGTH: 20
<212> TYPE: DNA
<213> ORGANISM: Artificial
<220> FEATURE:
<223> OTHER INFORMATION: primer

<400> SEQUENCE: 58
agcatgctct cggttgttct                                                20

<210> SEQ ID NO 59
<211> LENGTH: 20
<212> TYPE: DNA
<213> ORGANISM: Artificial
<220> FEATURE:
<223> OTHER INFORMATION: primer

<400> SEQUENCE: 59
gcacaccaag gagattgacc                                                20

<210> SEQ ID NO 60
<211> LENGTH: 20
<212> TYPE: DNA
<213> ORGANISM: Artificial
<220> FEATURE:
<223> OTHER INFORMATION: primer

<400> SEQUENCE: 60
tcccttctgg ttctgcaatc                                                20

<210> SEQ ID NO 61
<211> LENGTH: 20
<212> TYPE: DNA
<213> ORGANISM: Artificial
<220> FEATURE:
<223> OTHER INFORMATION: primer

<400> SEQUENCE: 61
tcggaactca tctccaggac                                                20

<210> SEQ ID NO 62
<211> LENGTH: 20
<212> TYPE: DNA
<213> ORGANISM: Artificial
<220> FEATURE:
<223> OTHER INFORMATION: primer

<400> SEQUENCE: 62
gccagagatg tagccacaag                                                20

<210> SEQ ID NO 63
<211> LENGTH: 20
<212> TYPE: DNA
<213> ORGANISM: Artificial
<220> FEATURE:
<223> OTHER INFORMATION: primer

<400> SEQUENCE: 63
tattgctaat gggggtggag                                                20

<210> SEQ ID NO 64
```

```
<211> LENGTH: 20
<212> TYPE: DNA
<213> ORGANISM: Artificial
<220> FEATURE:
<223> OTHER INFORMATION: primer

<400> SEQUENCE: 64
cagagcccac gatgacagta                                              20

<210> SEQ ID NO 65
<211> LENGTH: 20
<212> TYPE: DNA
<213> ORGANISM: Artificial
<220> FEATURE:
<223> OTHER INFORMATION: primer

<400> SEQUENCE: 65
gggggaacca ggcagtataa                                              20

<210> SEQ ID NO 66
<211> LENGTH: 20
<212> TYPE: DNA
<213> ORGANISM: Artificial
<220> FEATURE:
<223> OTHER INFORMATION: primer

<400> SEQUENCE: 66
taaacctggt ggtcctggag                                              20

<210> SEQ ID NO 67
<211> LENGTH: 20
<212> TYPE: DNA
<213> ORGANISM: Artificial
<220> FEATURE:
<223> OTHER INFORMATION: primer

<400> SEQUENCE: 67
ggaaaatctg gccattcaga                                              20

<210> SEQ ID NO 68
<211> LENGTH: 20
<212> TYPE: DNA
<213> ORGANISM: Artificial
<220> FEATURE:
<223> OTHER INFORMATION: primer

<400> SEQUENCE: 68
tgcgtggcac tcatactctc                                              20

<210> SEQ ID NO 69
<211> LENGTH: 20
<212> TYPE: DNA
<213> ORGANISM: Artificial
<220> FEATURE:
<223> OTHER INFORMATION: primer

<400> SEQUENCE: 69
agggagcaga cagagcagag                                              20

<210> SEQ ID NO 70
<211> LENGTH: 20
<212> TYPE: DNA
<213> ORGANISM: Artificial
<220> FEATURE:
<223> OTHER INFORMATION: primer

<400> SEQUENCE: 70
```
ctttgtcagg gagggtctca                                              20

<210> SEQ ID NO 71
<211> LENGTH: 20
<212> TYPE: DNA
<213> ORGANISM: Artificial
<220> FEATURE:
<223> OTHER INFORMATION: primer

<400> SEQUENCE: 71
cattgatggt gctggtgaac                                              20

<210> SEQ ID NO 72
<211> LENGTH: 21
<212> TYPE: DNA
<213> ORGANISM: Artificial
<220> FEATURE:
<223> OTHER INFORMATION: primer

<400> SEQUENCE: 72
tcatggacac aatcacagac c                                            21

<210> SEQ ID NO 73
<211> LENGTH: 20
<212> TYPE: DNA
<213> ORGANISM: Artificial
<220> FEATURE:
<223> OTHER INFORMATION: primer

<400> SEQUENCE: 73
gcgctgcaga tgtacgaata                                              20

<210> SEQ ID NO 74
<211> LENGTH: 21
<212> TYPE: DNA
<213> ORGANISM: Artificial
<220> FEATURE:
<223> OTHER INFORMATION: primer

<400> SEQUENCE: 74
ccattcttca gtgtggctat a                                            21

<210> SEQ ID NO 75
<211> LENGTH: 20
<212> TYPE: DNA
<213> ORGANISM: Artificial
<220> FEATURE:
<223> OTHER INFORMATION: primer

<400> SEQUENCE: 75
ttgtgtccac cttccacaaa                                              20

<210> SEQ ID NO 76
<211> LENGTH: 20
<212> TYPE: DNA
<213> ORGANISM: Artificial
<220> FEATURE:
<223> OTHER INFORMATION: primer

<400> SEQUENCE: 76
tggaatgcag cttcatctgt                                              20

<210> SEQ ID NO 77
<211> LENGTH: 20
<212> TYPE: DNA

```
<213> ORGANISM: Artificial
<220> FEATURE:
<223> OTHER INFORMATION: primer

<400> SEQUENCE: 77
caccacaggg ggattatttg                                               20

<210> SEQ ID NO 78
<211> LENGTH: 20
<212> TYPE: DNA
<213> ORGANISM: Artificial
<220> FEATURE:
<223> OTHER INFORMATION: primer

<400> SEQUENCE: 78
aggaagtcca ctgcttctgg                                               20

<210> SEQ ID NO 79
<211> LENGTH: 20
<212> TYPE: DNA
<213> ORGANISM: Artificial
<220> FEATURE:
<223> OTHER INFORMATION: primer

<400> SEQUENCE: 79
accagacatc caccaccatt                                               20

<210> SEQ ID NO 80
<211> LENGTH: 19
<212> TYPE: DNA
<213> ORGANISM: Artificial
<220> FEATURE:
<223> OTHER INFORMATION: primer

<400> SEQUENCE: 80
tcaggtgcag gcaaatagg                                                19

<210> SEQ ID NO 81
<211> LENGTH: 20
<212> TYPE: DNA
<213> ORGANISM: Artificial
<220> FEATURE:
<223> OTHER INFORMATION: primer

<400> SEQUENCE: 81
cagatgaacc atgctcagga                                               20

<210> SEQ ID NO 82
<211> LENGTH: 20
<212> TYPE: DNA
<213> ORGANISM: Artificial
<220> FEATURE:
<223> OTHER INFORMATION: primer

<400> SEQUENCE: 82
ctgtcctcca atggttaccg                                               20

<210> SEQ ID NO 83
<211> LENGTH: 24
<212> TYPE: DNA
<213> ORGANISM: Artificial
<220> FEATURE:
<223> OTHER INFORMATION: primer

<400> SEQUENCE: 83
acgagtggca gtttcttctt ggga                                          24
```

<210> SEQ ID NO 84
<211> LENGTH: 24
<212> TYPE: DNA
<213> ORGANISM: Artificial
<220> FEATURE:
<223> OTHER INFORMATION: primer

<400> SEQUENCE: 84
tatgactcac ttccaggggg cact                                          24

<210> SEQ ID NO 85
<211> LENGTH: 30
<212> TYPE: DNA
<213> ORGANISM: Artificial
<220> FEATURE:
<223> OTHER INFORMATION: primer

<400> SEQUENCE: 85
atggacgcaa ctgtgaacat gatgttcgca                                    30

<210> SEQ ID NO 86
<211> LENGTH: 30
<212> TYPE: DNA
<213> ORGANISM: Artificial
<220> FEATURE:
<223> OTHER INFORMATION: primer

<400> SEQUENCE: 86
ctttgaggtc ctggtccatc acgtgaccat                                    30

<210> SEQ ID NO 87
<211> LENGTH: 28
<212> TYPE: DNA
<213> ORGANISM: Artificial
<220> FEATURE:
<223> OTHER INFORMATION: primer

<400> SEQUENCE: 87
tgtggggccc tgaaaggcga gctgagat                                      28

<210> SEQ ID NO 88
<211> LENGTH: 28
<212> TYPE: DNA
<213> ORGANISM: Artificial
<220> FEATURE:
<223> OTHER INFORMATION: primer

<400> SEQUENCE: 88
atgggccgcc atacgacgac gctcaact                                      28

<210> SEQ ID NO 89
<211> LENGTH: 24
<212> TYPE: DNA
<213> ORGANISM: Artificial
<220> FEATURE:
<223> OTHER INFORMATION: primer

<400> SEQUENCE: 89
gaagtctggt tccttggcag gatg                                          24

<210> SEQ ID NO 90
<211> LENGTH: 20
<212> TYPE: DNA
<213> ORGANISM: Artificial
<220> FEATURE:

```
<223> OTHER INFORMATION: primer

<400> SEQUENCE: 90
actcgataca ctggcctagc                                               20

<210> SEQ ID NO 91
<211> LENGTH: 24
<212> TYPE: DNA
<213> ORGANISM: Artificial
<220> FEATURE:
<223> OTHER INFORMATION: primer

<400> SEQUENCE: 91
actgcccctc atcagactgc tact                                          24

<210> SEQ ID NO 92
<211> LENGTH: 24
<212> TYPE: DNA
<213> ORGANISM: Artificial
<220> FEATURE:
<223> OTHER INFORMATION: primer

<400> SEQUENCE: 92
cactgccttg tactcgggta gctg                                          24

<210> SEQ ID NO 93
<211> LENGTH: 23
<212> TYPE: DNA
<213> ORGANISM: Artificial
<220> FEATURE:
<223> OTHER INFORMATION: primer

<400> SEQUENCE: 93
cgtggtgagc atcttcggag tgg                                           23

<210> SEQ ID NO 94
<211> LENGTH: 23
<212> TYPE: DNA
<213> ORGANISM: Artificial
<220> FEATURE:
<223> OTHER INFORMATION: primer

<400> SEQUENCE: 94
ccttcttggt ccgcccgttc tta                                           23
```

CONTROL AGENT FOR CONTROLLING UNDIFFERENTIATED STATE AND USE THEREOF

TECHNICAL FIELD

The present invention relates to a control agent for controlling an undifferentiated state of undifferentiated cells and use thereof. More specifically, the present invention relates to a method for producing undifferentiated cells with their undifferentiated state being controlled and a method for controlling an undifferentiated state of undifferentiated cells, which are carried out using the above-described undifferentiated state-control agent.

BACKGROUND ART

Cells having pluripotency, such as ES cells and iPS cells, are undifferentiated cells. Owing to the pluripotency of the undifferentiated cells, the applicability of the undifferentiated cells to regenerative medicine etc. is attracting attention, and research and development regarding the undifferentiated cells now are being carried out eagerly. To this end, it is important to maintain the undifferentiated state of the undifferentiated cells during their culture.

Generally, the undifferentiated cells are cultured according to a culture method using feeder cells such as fibroblasts (so-called "on-feeder culture method"). In this method, feeder cells are cultured beforehand, and undifferentiated cells are then seeded on the feeder cells. Also, in recent years, a culture method without involving the use of feeder cells is developed, which is a so-called "feeder free culture method". In the feeder free culture method, a serum-free medium is used, for example (Patent Documents 1 to 5, Non-Patent Documents 1 to 14).

However, these known culture methods cannot maintain the pluripotency and the undifferentiated state of the undifferentiated cells sufficiently. For example, in the case of mouse-derived pluripotent stem cells, LIF (Leukemia Inhibitory Factor) is added to a medium as a differentiation inhibitory factor. However, sufficient maintenance of the pluripotency and the undifferentiated state cannot be realized merely by adding LIF. Moreover, for human-derived pluripotent stem cells, effective means for maintaining and/or improving the pluripotency and the undifferentiated state thereof have not been established yet.

CITATION LIST

Patent Document(s)

Patent Document 1: JP 2001-17163 A
Patent Document 2: JP 2006-345702 A
Patent Document 3: JP 2006-204292 A
Patent Document 4: JP 2009-72186 A
Patent Document 5: JP 2010-004796 A

Non-Patent Document(s)

Non-Patent Document 1: Thomson J A et al., Proc. Natl. Acad. Sci. USA (1995) 92, 7844-7848
Non-Patent Document 2: Thomson J A et al., Science, (1998) 282, 1145-1147
Non-Patent Document 3: Reubinoff B E et al., Nat Biotechnol, (2000)18, 399-404.
Non-Patent Document 4: Xu C, et al., Nat Biotechnol (2001) 19, 971-974.
Non-Patent Document 5: Amit M, et al., Biol Reprod (2004) 70, 837-845.
Non-Patent Document 6: Chambers I. et al., Cell (2003) 113, 643-655.
Non-Patent Document 7: Mitsui K. et al., Cell (2003) 113, 631-642.
Non-Patent Document 8: Ying Q. L. et al., Cell (2003) 115, 281-292.
Non-Patent Document 9: Mitalipova M et al., Stem Cells (2003) 21, 521-526.
Non-Patent Document 10: Heins N et al., Stem Cells, (2004) 22, 367-376.
Non-Patent Document 11: Sato N et al., Nature Medicine, (2004) 10, 55-63.
Non-Patent Document 12: Beattie G M, et al., Stem Cells (2005) 23, 489-495.
Non-Patent Document 13: Boiani, M. et al., Nat Rev Mol Cell Biol. (2005) 6, 872-884
Non-Patent Document 14: Totonchi M, et al., Int J Dev Biol. (2010) 54, 877-886.

BRIEF SUMMARY OF THE INVENTION

With the foregoing in mind, it is an object of the present invention to provide a novel undifferentiated state-control agent that maintains and/or improves an undifferentiated state of undifferentiated cells, and use thereof.

In order to achieve the above object, the present invention provides a control agent for controlling an undifferentiated state of an undifferentiated cell, containing: CCL2 or a protein containing a functional domain of the CCL2.

The present invention also provides a method for producing an undifferentiated cell with its undifferentiated state being controlled. The method includes the step of culturing the undifferentiated cell in the presence of the control agent according to the present invention.

The present invention also provides a method for controlling an undifferentiated state of an undifferentiated cell. The method includes the step of culturing the undifferentiated cell by the production method of the present invention, thereby maintaining and/or improving the undifferentiated state of the undifferentiated cell.

According to the present invention, CCL2 or a protein containing a functional domain of the CCL2 can maintain and/or improve an undifferentiated state of undifferentiated cells. According to the present invention, it is possible to culture undifferentiated cells such as ES cells and iPS cells with their undifferentiated state being maintained and/or improved, for example. Thus, the present invention is particularly useful for various medical applications including regenerative medicine and research thereon.

BRIEF DESCRIPTION OF DRAWINGS

FIG. 5 shows the results indicating the phosphorylation of STAT3 in mouse iPS cells in the presence of CCL2 in still another example of the present invention.

FIG. 6 shows the result indicating the phosphorylation of AKT in mouse iPS cells in the presence of CCL2 in still another example of the present invention.

FIG. 7 shows the result indicating the phosphorylation of ERK1/2 in mouse iPS cells in the presence of CCL2 in the example of the present invention. FIG. 7A shows photographs showing the results of Western blotting. FIG. 7B is a graph showing the ratio of phosphorylated ERK1/2 to non-phosphorylated ERK1/2.

FIG. 8 is a graph showing the results of the flow cytometry analysis with respect to mouse iPS cells expressing the Nanog gene as an undifferentiated marker gene in the example of the present invention FIG. 9 is a graph showing the expression level of the Tbx3 gene as an undifferentiated marker gene in mouse iPS cells in the presence of CCL2 in the example of the present invention.

FIG. 15 shows the result indicating the phosphorylation of STAT3 and AKT in human iPS cells in the presence of a CCL2 protein in still another example of the present invention. FIG. 15A shows photographs showing the results of Western blotting. FIG. 15B is a graph showing the ratio of phosphorylated STAT3 to non-phosphorylated STAT3. FIG. 15C is a graph showing the ratio of phosphorylated AKT to non-phosphorylated AKT. FIG. 15D is a graph showing the ratio of KLF4 gene expression to GAPDH gene expression.

FIG. 18 shows photographs showing the morphologies of EBs produced from human iPS cells after spontaneous differentiation-inducing culture in still another example of the present invention.

FIG. 19 shows photographs showing the morphologies of EBs produced from human iPS cells after culture in the example of the present invention.

FIG. 20 shows photographs showing the morphologies of EBs produced from human iPS cells after spontaneous differentiation-inducing culture in still another example of the present invention.

MODE FOR CARRYING OUT THE INVENTION

Figure 1:
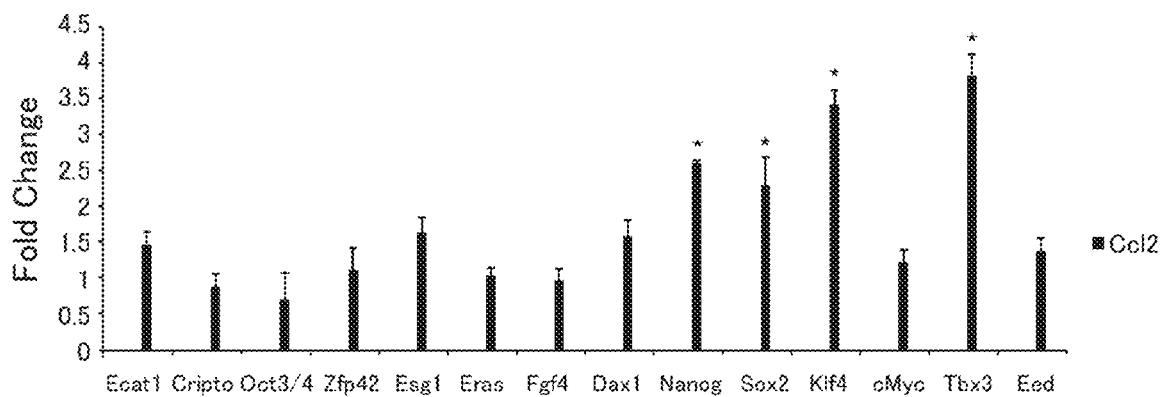
FIG. 1 is a graph showing the fold changes in expression of undifferentiated marker genes in mouse iPS cells in which CCL2 was overexpressed in an example of the present invention.

The present invention will be described with reference to the following first and seconds embodiments. It is to be noted that the present invention is by no means limited to these embodiments.

(First Embodiment)
(1) First Control Agent

A first control agent according to the present invention is a control agent for controlling an undifferentiated state of undifferentiated cells, containing CCL2 or a protein containing a functional domain of the CCL2, as described above. The first control agent according to the present invention maintains and/or improves the undifferentiated state of undifferentiated cells. The first control agent according to the present invention also can be referred to as an undifferentiated state-maintaining agent or an undifferentiated state-improving agent, and also can be denoted as a "maintenance-improvement agent", for example.

In the present invention, the expression such as "maintaining the undifferentiated state" means, for example, to allow undifferentiated cells to maintain the undifferentiated state (differentiation hierarchy) that they have exhibited in the absence of the control agent. In the present invention, the expression such as "improving the undifferentiated state" means to cause the undifferentiated state (the hierarchy) of undifferentiated cells to shift toward a more undifferentiated state than that in the absence of the control agent, i.e., promoting dedifferentiation, and it also is referred to as improving the undifferentiation potency (hereinafter the same).

Furthermore, according to the control agent of the present invention, it is also possible to promote the adhesion and/or growth of undifferentiated cells, for example. Thus, the control agent of the present invention also can be referred to as an agent for promoting the adhesion and/or growth of undifferentiated cells, for example. The agent for promoting the adhesion and/or growth of undifferentiated cells according to the present invention is characterized in that it contains CCL2 or a protein containing a functional domain of the CCL2, and the following description regarding the control agent according to the present invention can be referenced. Furthermore, a method for controlling an undifferentiated state of undifferentiated cells according to the present invention also can be referred to as a method for promoting the adhesion and/or growth of undifferentiated cells, for example. The method for promoting the adhesion and/or growth of undifferentiated cells according to the present invention has the same configuration as the method for controlling an undifferentiated state of undifferentiated cells according to the present invention to be described below, and the description regarding the control method can be referenced.

CCL2, which is C-C motif chemokine 2, is a protein classified in the CXC family. In the present invention, CCL2 means a protein having a function of CCL2, and a functional domain of CCL2 means a domain that contributes to a CCL2 function in CCL2. A protein that contains the functional domain of CCL2 hereinafter is referred to as a "CCL2-like protein".

In the present invention, the function of CCL2 means a function of maintaining and/or improving an undifferentiated state of undifferentiated cells. The function of CCL2 also can be referred to as a function of inducing the chemotaxis of monocytes and the like, for example.

The control agent according to the present invention may contain either one of the CCL2 and the CCL2-like protein, or may contain both of them, for example. The control agent according to the present invention may contain, as an active ingredient(s), only the CCL2, only the CCL2-like protein, or both the CCL2 and the CCL2-like protein, for example.

The kind of the CCL2 is not particularly limited. The origin of the CCL2 is not particularly limited, and examples thereof include mammals. Examples of the mammals include humans and nonhuman mammals. Examples of the nonhuman mammals include: primates such as monkeys; mice; chickens; horses; rats; pigs; and rabbits. The CCL2 may be a natural product, or may be a synthesized product synthesized artificially, for example. The method for synthesizing the synthesized product is not particularly limited, and may be a genetic engineering procedure, for example. Specific examples thereof include: protein synthesis using cells; and cell-free protein synthesis that does not use cells. The CCL2 may be a natural CCL2 or a modified protein obtained by modifying the natural CCL2, for example. The modified protein as the latter may be, for example, a protein having an amino acid sequence obtained by deletion, substitution, insertion, and/or addition of one or more amino acids in the amino acid sequence of the natural CCL2, or may be a protein having an amino acid sequence obtained by modification of one or more amino acids in the amino acid sequence of the natural CCL2. Such proteins are encompassed in CCL2 in the present invention as long as they have the function of CCL2.

In the present invention, as well as the CCL2, a protein containing a functional domain of CCL2 (the CCL2-like protein) similarly can be used. In this case, the CCL2-like protein is not limited as long as the functional domain of the CCL2 contained therein exhibits its function, for example, and other conditions are by no means limited. Specifically, other conditions of the CCL2-like protein, such as, for example, the sequence other than the functional domain, are by no means limited. The CCL2-like protein may be a protein consisting of polypeptides forming the functional domain, or a protein containing polypeptides forming the functional domain, for example.

Examples of the amino acid sequences of CCL2 and the functional domain thereof are shown below. It is to be noted, however, that the present invention is not limited to these examples.

The CCL2 or the CCL2-like protein is any one of the following proteins (A1), (A2), (A3), (B1), (B2), and (B3), for example.

(A1) a protein having an amino acid sequence of SEQ ID NO: 1:

```
SEQ ID NO: 1:
MKVSAALLCLLLIAATFIPQGLAQPDAINAPVTCCYNFTNRKISVQRLA

SYRRITSSKCPKEAVIFKTIVAKEICADPKQKWVQDSMDHLDKQTQTPK

T
```

(A2) a protein having an amino acid sequence obtained by deletion, substitution, insertion, and/or addition of one or more amino acids in the amino acid sequence of SEQ ID NO: 1 and having a function of the CCL2

(A3) a protein having an amino acid sequence with an identity of at least 80% to the amino acid sequence of SEQ ID NO: 1 and having a function of the CCL2

(B1) a protein having an amino acid sequence of SEQ ID NO: 3:

```
SEQ ID NO: 3:
MQVPVMLLGLLFTVAGWSIHVLAQPDAVNAPLTCCYSFTSKMIPMSRLE

SYKRITSSRCPKEAVVFVTKLKREVCADPKKEWVQTYIKNLDRNQMRSE

PTTLFKTASALRSSAPLNVKLTRKSEANASTTFSTTTSSTSVGVTSVTV

N
```

(B2) a protein having an amino acid sequence obtained by deletion, substitution, insertion, and/or addition of one or more amino acids in the amino acid sequence of SEQ ID NO: 3 and having a function of the CCL2

(B3) a protein having an amino acid sequence with an identity of at least 80% to the amino acid sequence of SEQ ID NO: 3 and having a function of the CCL2.

The protein (A1) is human CCL2. The amino acid sequence of SEQ ID NO: 1 is the full-length amino acid sequence of the CCL2, and is registered under SWISSPROT Acc. No. P13500, for example. In the amino acid sequence of SEQ ID NO: 1, a region extending from the 24th amino acid to 99th amino acid is the functional domain of the CCL2, for example.

In the protein (A2), the number of amino acids to be subjected to deletion etc. is not particularly limited, and is, for example, one or a few, preferably 1 to 10, more preferably 1 to 5, still more preferably 1 to 3, and particularly preferably 1 or 2.

In the protein (A3), the identity is not particularly limited, and is, for example, at least 80%, more preferably at least 90%, still more preferably at least 95%, at least 96%, at least 97%, and at least 98%, and particularly preferably at least 99%. The identity can be calculated using BLAST or the like under default conditions, for example (hereinafter the same).

The protein (B1) is mouse CCL2. The amino acid sequence of SEQ ID NO: 3 is the full-length amino acid sequence of the CCL2, and is registered under SWISSPROT Acc. No. P10148 or NP_035463.1, for example. In the amino acid sequence of SEQ ID NO: 3, a region extending from the 24th amino acid to the 148th amino acid is the functional domain of the CCL2, for example.

In the protein (B2), the number of amino acids to be subjected to deletion etc. is not particularly limited, and is, for example, one or a few, preferably 1 to 10, more preferably 1 to 5, still more preferably 1 to 3, and particularly preferably 1 or 2.

In the protein (B3), the identity is not particularly limited, and is, for example, at least 80%, more preferably at least 90%, still more preferably at least 95%, at least 96%, at least 97%, and at least 98%, and particularly preferably at least 99%.

The CCL2 or the CCL2-like protein is, for example, a protein having, as the functional domain of the CCL2, any one of the following polypeptides (A1'), (A2'), (A3'), (B1'), (B2'), and (B3').

(A1') a polypeptide having an amino acid sequence of SEQ ID NO: 2:

```
SEQ ID NO: 2:
QPDAINAPVTCCYNFTNRKISVQRLASYRRITSSKCPKEAVIFKTIVAK
EICADPKQKWVQDSMDHLDKQTQTPKT
```

(A2') a polypeptide having an amino acid sequence obtained by deletion, substitution, insertion, and/or addition of one or more amino acids in the amino acid sequence of SEQ ID NO: 2 and having a function of the CCL2

(A3') a polypeptide having an amino acid sequence with an identity of at least 80% to the amino acid sequence of SEQ ID NO: 2 and having a function of the CCL2

(B1') a polypeptide having an amino acid sequence of SEQ ID NO: 4:

```
SEQ ID NO: 4:
QPDAVNAPLTCCYSFTSKMIPMSRLESYKRITSSRCPKEAVVFVTKLKR
EVCADPKKEWVQTYIKNLDRNQMRSEPTTLFKTASALRSSAPLNVKLTR
KSEANASTTFSTTTSSTSVGVTSVTVN
```

(B2') a polypeptide having an amino acid sequence obtained by deletion, substitution, insertion, and/or addition of one or more amino acids in the amino acid sequence of SEQ ID NO: 4 and having a function of the CCL2

(B3') a polypeptide having an amino acid sequence with an identity of at least 80% to the amino acid sequence of SEQ ID NO: 4 and having a function of the CCL2.

The polypeptide (A1') is a functional domain of human CCL2. The amino acid sequence of SEQ ID NO: 2 corresponds to the region extending from the 24th amino acid to 99th amino acid in the amino acid sequence of SEQ ID NO: 1, for example.

In the polypeptide (A2'), the number of amino acids to be subjected to deletion etc. is not particularly limited, and is, for example, one or a few, preferably 1 to 10, more preferably 1 to 5, still more preferably 1 to 3, and particularly preferably 1 or 2.

In the polypeptide (A3'), the identity is not particularly limited, and is, for example, at least 80%, more preferably at least 90%, still more preferably at least 95%, at least 96%, at least 97%, and at least 98%, and particularly preferably at least 99%.

The polypeptide (B1') is the functional domain of mouse CCL2, and the amino acid sequence of SEQ ID NO: 4 corresponds to, e.g., a region extending from the 24th amino acid to the 148th amino acid in, e.g., the amino acid sequence of SEQ ID NO: 3.

In the polypeptide (B2'), the number of amino acids to be subjected to deletion etc. is not particularly limited, and is, for example, one or a few, preferably 1 to 10, more preferably 1 to 5, still more preferably 1 to 3, and particularly preferably 1 or 2.

In the polypeptide (B3'), the identity is not particularly limited, and is, for example, at least 80%, more preferably at least 90%, still more preferably at least 95%, at least 96%, at least 97%, and at least 98%, and particularly preferably at least 99%.

The subject to which the control agent of the present invention is applied is not particularly limited. In the present invention, the differentiation stage, i.e., the hierarchy, of undifferentiated cells is not particularly limited, and the undifferentiated cells may be in any differentiation stage prior to the fully differentiated stage. The undifferentiated cells are cells that are expressing undifferentiated marker genes, for example. The undifferentiated state of cells can be determined using their undifferentiated marker genes as indicators, for example. Examples of the undifferentiated marker genes include Klf4, Nanog, Tbx3, Rex1, and Stella. These genes are marker genes indicating the blastocyst state (naive pluripotent state), which is a more undifferentiated state, for example. The undifferentiated cells also can be referred to as cells that are in an undifferentiated state where they exhibit replication competence and pluripotency, for example.

The undifferentiated cells may be, for example, cells derived from an embryo or from a tissue of a living organism, or may be artificially-produced undifferentiated cells. Examples of the undifferentiated cells that are in a more undifferentiated state include embryonic stem cells (ES cells) and embryonic germ cells (EG cells). Examples of the undifferentiated cells that are in a more differentiated state include somatic stem cells (also referred to as adult stem cells). Examples of the somatic stem cells include pluripotent adult stem cells (also referred to as multipotent adult progenitor cells), hematopoietic stem cells, vascular endothelial stem cells, mesenchymal stem cells, hepatic stem cells, neural stem cells, epithelial stem cells, and pancreatic stem cells, and hepatic stem cells. Examples of the undifferentiated cells further include primordial germ cells. Still further examples of the undifferentiated cells include embryonal carcinoma cells (EC cells). Examples of the artificial undifferentiated cells include nuclear transfer embryonic stem cells (ntES cell). Furthermore, as the artificial undifferentiated cells, it is possible to use, for example, induced pluripotent stem cells (iPS cell), which are cells having pluripotency imparted by gene transfer, a treatment with a compound, or the like (e.g., WO 2007/069666, JP 2010-273680 A, JP 2010-284088 A, JP 2011-50379 A, and JP 2011-4674 A).

The origin of the undifferentiated cells is not particularly limited, and the undifferentiated cells may be derived from mammals, for example. Examples of the mammals include humans and nonhuman mammals. Examples of the nonhuman mammals include: primates such as monkeys; mice; chickens; horses; rats; pigs; and rabbits.

The origin of the CCL2 or the CCL2-like protein in the control agent of the present invention may be the same as or different from the origin of the undifferentiated cells, for example. When the origins of them are the same, they preferably are derived from a mammal, more preferably a primate or a rodent, and still more preferably a human or a mouse, for example.

In the control agent of the present invention, the CCL2 and the CCL2-like protein may have any other peptide bound thereto, as long as they exhibit a function of the CCL2. The number and the kind of amino acid residues in the other peptide are not particularly limited.

The control agent of the present invention further may contain a component other than the CCL2 and/or the CCL2-like protein. The other component is not particularly limited, and examples thereof include components contained in a medium to be described below.

The control agent of the present invention can maintain the differentiation hierarchy that the undifferentiated cells have exhibited in the absence of the control agent of the present invention, for example. Thus, the control agent of the present invention also can be referred to as a differentiation hierarchy-maintaining agent. Generally, the hierarchy of the undifferentiated cells proceeds from undifferentiated blastocysts (naive pluripotent state) to more differentiated epiblasts (primed pluripotent state). Thus, the control agent of the present invention also can be referred to as a blastocyst state-maintaining agent or an inhibitor for inhibiting differentiation into epiblasts, for example. Moreover, according to the control agent of the present invention, it is possible to promote the progression of dedifferentiation from epiblasts to blastocysts, especially in human-derived undifferentiated cells, for example. Thus, the control agent of the present invention also can be referred to as a differentiation hierarchy-improving agent or a dedifferentiation-promoting agent, for example.

The form of the control agent of the present invention is not particularly limited. The control agent of the present invention further may include a medium, so that it serves as a medium for controlling an undifferentiated state of the undifferentiated cells, for example, as will be described below. Also, the control agent of the present invention further may include a culture container, so that it serves as a culture container for controlling an undifferentiated state of the undifferentiated cells, with the CCL2 or the CCL2-like protein being immobilized on the culture container beforehand. In the latter case, for example, there is no need to add the control agent to a medium each time culture is performed, so that it is possible to maintain the CCL2 or the CCL2-like protein stably. Furthermore, by immobilizing the CCL2 or the CCL2-like protein on the culture container, it is possible to provide a scaffold for cells to be cultured, for example. The culture container is not particularly limited, and examples thereof include flasks, dishes, and well plates. The method for immobilizing the CCL2 and the CCL2-like protein is not particularly limited as long as the above-described function of the CCL2 and the CCL2-like protein is maintained, and any known method can be employed as appropriate. Regarding the method for achieving the immobilization, Nature Methods Vol. 5, No. 7, 2008, pp. 645-650 and the like can be referenced, for example.

The method for using the control agent of the present invention will be described, for example, in connection with a medium for controlling an undifferentiated state of undifferentiated cells according to the present invention to be described below.

(2) First Medium for Controlling Undifferentiated State of Undifferentiated Cells A first medium for controlling an undifferentiated state of undifferentiated cells according to the present invention is, as described above, a medium for culturing the undifferentiated cells, and corresponds to one form of the control agent of the present invention.

As long as the medium of the present invention contains the control agent of the present invention, other configurations and conditions of the medium are by no means limited. The medium of the present invention may be, for example, a basal medium containing the control agent, which can be prepared by adding the control agent to the basal medium.

In the medium of the present invention, the content of the control agent is not particularly limited. When the control agent contains the CCL2 as an active ingredient, the lower limit of the CCL2 concentration in the medium is, for example, 500 ng/ml, preferably 1000 ng/ml, and more preferably 2000 ng/ml, and particularly preferably 2500 ng/ml. The upper limit of the CCL2 concentration in the medium is, for example, 10000 ng/ml, preferably 8000 ng/ml, more preferably 5000 ng/ml, and particularly preferably 2500 ng/ml. The CCL2 concentration in the medium is in the range from, for example, 500 ng/ml to 10000 ng/ml, preferably 1000 ng/ml to 8000 ng/ml, and particularly preferably 2000 ng/ml to 5000 ng/ml. When the control agent contains the CCL2-like protein as an active ingredient, the CCL2-like protein concentration in the medium is not particularly limited, and may be the same as the above-described concentration of the CCL2 added to the medium, for example. The CCL2-like protein concentration can be converted from the concentration of the CCL2 added to the medium based on the amount of the functional domain.

The medium of the present invention further may contain any other differentiation inhibitory factor, for example. Examples of the differentiation inhibitory factor include LIF (leukemia inhibitory factor), bFGF, NODAL, and a GSK/MEK inhibitor. The LIF preferably is used in media for mouse-derived cells, for example. The bFGF and NODAL preferably are used in media for human-derived cells. The origin of the differentiation inhibitory factor is not particularly limited, and may be the same as or different from the origin of the undifferentiated cells to be cultured, for example. When the undifferentiated cells are derived from a rodent such as a mouse or a rat, LIF can be used as the differentiation inhibitory factor, for example. The differentiation inhibitory factor may be the one that occurs naturally, or may be prepared artificially by transformation or the like, for example.

Heretofore, when undifferentiated cells derived from a rodent are cultured, LIF generally is added to a medium as a differentiation inhibitory factor. However, according to the medium of the present invention, the undifferentiated state of the undifferentiated cells can be maintained and/or improved by the CCL2 and/or the CCL2-like protein, even when the medium does not contain LIF, for example. The medium of the present invention further may contain LIF, for example. When the medium of the present invention further contains LIF, the undifferentiated state of the undifferentiated cells can be maintained and/or improved still further, for example.

When the medium of the present invention further contains any of the above-described other differentiation inhibitory factors, the content thereof is not particularly limited. When the differentiation inhibitory factor is LIF, the lower limit of the LIF concentration in the medium is, for example, 25 units/ml, preferably 50 units/ml, more preferably 100 units/ml, and particularly preferably 200 units/ml. The upper limit of the LIF concentration in the medium is, for example, 1000 units/ml, preferably 800 units/ml, more preferably 500 units/ml, and particularly preferably 300 units/ml. The LIF concentration in the medium is in the range from, for example, 25 units/ml to 1000 units/ml, preferably 50 units/ml to 800 units/ml, more preferably 100 units/ml to 500 units/ml, and particularly preferably 200 units/ml to 300 units/ml. The unit of LIF is as follows: when the amount of LIF necessary for inhibiting the differentiation of ES cells is defined as 1000 units/ml, 1 unit of LIF corresponds to one-thousandth thereof, for example.

When the medium of the present invention contains LIF, the ratio between the CCL2 and/or the CCL2-like protein and the LIF in the medium is not particularly limited. In the medium, for example, with respect to 1 ng of the CCL2 and/or the CCL2-like protein, it is preferable that the LIF is present in an amount in the range from 0.1 units/ml to 2 units/ml, more preferably 0.1 units/ml to 1.5 units/ml, still more preferably 0.1 units/ml to 1 unit/ml, and particularly preferably 0.1 units/ml to 0.5 units/ml.

The medium of the present invention further may contain a growth factor, for example. Examples of the growth factor include bFGF (basic Fibroblast Growth Factor) and TGFβ (transforming growth factor-beta). The origin of the growth factor is not particularly limited, and may be the same as or different from the origin of the undifferentiated cells to be cultured, for example. When the undifferentiated cells are human-derived cells, bFGF can be used as the growth factor, for example. The growth factor may be one that occurs naturally, or may be prepared artificially by transformation or the like, for example.

When the medium of the present invention further contains the growth factor, the content thereof is not particularly limited. When the growth factor is bFGF, the lower limit of the bFGF concentration in the medium is, for example, 4 ng/ml, preferably 5 ng/ml, more preferably 8 ng/ml, and particularly preferably 10 ng/ml. The upper limit of the bFGF concentration in the medium is, for example, 20 ng/ml, preferably 17 ng/ml, more preferably 15 ng/ml, and particularly preferably 10 ng/ml. The bFGF concentration in the medium is in the range from, for example, 4 ng/ml to 20 ng/ml, preferably 5 ng/ml to 17 ng/ml, more preferably 8 ng/ml to 15 ng/ml, and particularly preferably about 4 ng/ml or about 10 ng/ml.

When the medium of the present invention contains bFGF, the ratio between the CCL2 and/or the CCL2-like and the bFGF in the medium is not particularly limited. In the medium, for example, with respect to 1 ng of the CCL2 and/or the CCL2-like protein, it is preferable that the bFGF is present in an amount in the range from 0.016 ng/ml to 0.04 ng/ml or 0.02 ng/ml to 0.04 ng/ml, more preferably 0.016 ng/ml to 0.034 ng/ml, still more preferably 0.016 ng/ml to 0.03 ng/ml, and particularly preferably about 0.02 ng/ml.

The medium of the present invention can be prepared by adding the CCL2 and/or the CCL2-like protein to a basal medium, for example. The basal medium is not particularly limited as long as it contains components necessary for culture, components necessary for growth, and the like, and can be set as appropriate depending on the kind of undifferentiated cells to be cultured, for example. Examples of the basal medium include Doulbecco Modified Eagle's Medium (DMEM) and KnockOut DMEM (KO DMEM). Also, as the basal medium, it is possible to use a known on-feeder medium, a feeder-free medium, or the like. Whether or not the basal medium contains the above-described other differentiation inhibitory factor such as LIF and whether or not the basal medium contains the growth factor such as bFGF are not particularly limited, and may be as described above. The basal medium may contain, for example: serum such as fetal bovine serum (FBS); an essential amino acid; a growth cofactor such as a non-essential amino acid; nucleoside; and β mercaptoethanol.

The pH of the medium of the present invention is not particularly limited, and can be set as appropriate depending on the kind of the undifferentiated cells to be cultured, for example. The pH of the medium is, for example, 6 to 7, preferably 6.5 to 7, and more preferably 6.8 to 7.

The medium of the present invention may be, for example, a medium (hereinafter referred to as "on-feeder medium") for culture using feeder cells (hereinafter referred to as "on-feeder culture"), or may be a medium (hereinafter referred to as "feeder-free medium") for culture without using feeder cells (hereinafter referred to as "feeder free culture"). In the present invention, the basal medium can be selected as appropriate depending on the kind of the on-feeder culture and feeder free culture, the kind of cells to be cultured, etc., for example. Examples of the basal medium will be given below. It is to be noted, however, that the present invention is not limited thereto.

When undifferentiated mouse cells are cultured in an on-feeder medium, the basal medium can be, for example, a serum-added medium or a serum-free medium (medium containing no serum), and preferably is the serum-added medium. The kind of the serum is not particularly limited, and FBS or the like can be used. When undifferentiated human cells are cultured in an on-feeder medium, the basal medium preferably is a serum-free medium, for example.

When undifferentiated mouse cells are cultured in a feeder-free medium, the basal medium preferably is the serum-added medium, for example. The kind of the serum is not particularly limited, and FBS or the like can be used. When undifferentiated human cells are cultured in a feeder-free medium, the basal medium preferably is a serum-free medium, for example.

The method for using the medium of the present invention will be described below, for example, in connection with the production method of the present invention.

(3) First Method for Producing Undifferentiated Cells with their Undifferentiated State being Controlled A first method for producing undifferentiated cells with their undifferentiated state being controlled according to the present invention is characterized in that it includes the step of culturing the undifferentiated cells in the presence of the undifferentiated state-control agent according to the present invention.

As long as the production method of the present invention includes the step of culturing undifferentiated cells in the presence of the control agent of the present invention, other steps and conditions of the production method are by no means limited. In the production method of the present invention, the above-described culture step preferably is the step of culturing the undifferentiated cells using the medium for controlling an undifferentiated state of undifferentiated cells according to the present invention, which contains the above-described control agent.

In the production method of the present invention, the origin of the CCL2 or the CCL2-like protein provided by the control agent may be the same as or different from the origin of the undifferentiated cells to be cultured, for example. Preferably, the origin of the CCL2 or the CCL2-like protein and the origin of the undifferentiated cell are the same. More preferably, they are both mammals. Still more preferably, they are both the same mammal. Specifically, when human-derived undifferentiated cells are cultured, it is preferable to use the CCL2 and/or the CCL2-like protein derived from a human, and when mouse-derived undifferentiated cells are cultured, it is preferable to use the CCL2 and/or the CCL2-like protein derived from a mouse.

The kind of the undifferentiated cells to be cultured is not particularly limited, and may be any of the above-described various cells. The method for preparing the undifferentiated cells is not particularly limited. The undifferentiated cells can be collected and prepared according to any known method.

The culture in the production method of the present invention may be either on-feeder culture or feeder free culture, for example. By culturing undifferentiated cells in the presence of the control agent of the present invention, for example, an undifferentiated state of the undifferentiated cells can be maintained and/or improved effectively either in on-feeder culture or in feeder free culture.

When on-feeder culture is employed in the production method of the present invention, the feeder cells are not particularly limited, and any known feeder cells can be used. The feeder cells generally mean another type of cells used to adjust the culture conditions when growing target cells. The kind of the feeder cells is not particularly limited, and can be determined as appropriate depending on the kind of the undifferentiated cells to be cultured, for example. Examples of the feeder cells include fibroblasts and SNL cells. Preferably, the feeder cells are fetus-derived cells. The origin of the feeder cells may be the same as or different from the origin of the undifferentiated cells, for example. When the origins of them are the same, they preferably are derived from, for example, a mammal, more preferably a primate or a rodent, and still more preferably a human or a mouse.

In the production method of the present invention, the culture conditions are not particularly limited, and can be set as appropriate depending on the kind of the undifferentiated cells to be cultured. In the culture, the $O_2$ partial pressure preferably is 1% to 21%, for example, and the $CO_2$ partial pressure preferably is 5% to 6%, for example. The culture temperature preferably is 36° C. to 37° C., for example.

(4) First Undifferentiated State-Control Method

A first undifferentiated state-control method according to the present invention is a method for controlling an undifferentiated state of the undifferentiated cells, including the step of culturing the undifferentiated cells according to the first production method of the present invention. By culturing the undifferentiated cells according to the first production method of the present invention, the undifferentiated state of the undifferentiated cells can be maintained and/or improved.

As long as the control method of the present invention includes the step of culturing the undifferentiated cells according to the first production method of the present invention, other steps and conditions of the control method are by no means limited. As to the control method of the present invention, the description regarding the first production method of the present invention can be referenced to, for example.

By the control method of the present invention, for example, it is possible to maintain the differentiation hierarchy that the undifferentiated cells have exhibited in the absence of the control agent of the present invention. Thus, the control method of the present invention also can be referred to as a method for maintaining the differentiation hierarchy. Generally, the hierarchy of the undifferentiated cells proceeds from blastocysts to epiblasts. Thus, the control method of the present invention also can be referred to as a method for maintaining a blastocyst state or a method for inhibiting differentiation into epiblasts, for example. Moreover, according to the control method of the present invention, for example, it is possible to promote the progression of dedifferentiation from epiblasts to blastocysts, especially in human-derived undifferentiated cells, for example. Thus, the control method of the present invention also can be referred to as a method for improving the differentiation hierarchy or a method for promoting dedifferentiation, for example.

Undifferentiated cells with their undifferentiated state being maintained and/or improved by the production method or the control method according to the present invention can be caused to differentiate to desired cells by inducing differentiation at any desired timing, for example. The method for inducing differentiation is not particularly limited, and any conventionally known method can be employed. Examples of the method include spontaneous differentiation-inducing method that induces spontaneous differentiation by forming embryonic bodies (EB) and then culturing them in a serum-containing medium on a gelatin coated dish. When the undifferentiated cells are subjected to differentiation induction, the undifferentiated cells preferably are cultured in the absence of the CCL2 or the CCL2-like protein, for example.

Second Embodiment (1) Second Control Agent

Next, the second control agent of the present invention is a control agent for controlling an undifferentiated state of undifferentiated cells, which is characterized in that it contains an expression vector that expresses the CCL2 or a protein containing a functional domain of the CCL2 (the CCL2-like protein). The second control agent of the present invention can cause the expression of the CCL2 or the CCL2-like protein. Thus, for example, by using this expression product in the culture of the undifferentiated cells, it is possible to maintain and/or improve the undifferentiated state of the undifferentiated cells.

Furthermore, according to the control agent of the present invention, for example, it is also possible to promote the cell adhesion and/or growth while maintaining and/or improving the undifferentiated state of the undifferentiated cells. Thus, the control agent of the present invention can be referred to as an agent for promoting adhesion and/or growth of undifferentiated cells, for example. The agent for promoting adhesion and/or growth of undifferentiated cells according to the present invention is characterized in that it contains the expression vector, and the following description regarding the control agent of the present invention can be referenced. Furthermore, the method for controlling the undifferentiated state of undifferentiated cells according to the present invention also can be referred to as a method for promoting adhesion and/or growth of undifferentiated cells, for example. The method for promoting adhesion and/or growth of undifferentiated cells according to the present invention has the same configuration as the method for controlling an undifferentiated state of undifferentiated cells according to the present invention to be described below, and the description regarding the control method can be referenced.

The expression vector is not limited as long as at least one of the coding sequence of the CCL2 and the coding sequence of the CCL2-like protein is inserted thereto in an expressible manner. Specifically, the expression vector is not limited as long as it can cause the expression of the CCL2 or the CCL2-like protein in a cell transfected with the expression vector, for example. The expression vector may be configured so that, for example: only the coding sequence of the CCL2 is inserted thereto; only the coding sequence of the CCL2-like protein is inserted thereto; or both the coding sequence of the CCL2 and the coding sequence of the CCL2-like protein are inserted thereto.

The coding sequence of the CCL2 and the coding sequence of the CCL2-like protein are not particularly limited. Each coding sequence can be designed by conversion from the above-described amino acid sequences to codons corresponding thereto, for example. Examples of the coding DNA sequences of the CCL2 and the CCL2-like protein are shown below. It is to be noted, however, that the present invention is not limited thereto.

The coding sequence of the CCL2 or the CCL2-like protein is a DNA having any one of the following polynucleotides (a1), (a2), (a3), (a4), (b1), (b2), (b3), and (b4). Also, the coding sequence of the CCL2 or the CCL2-like protein may be a DNA having a polynucleotide complementary to any of the above polynucleotides.

(a1) a polynucleotide having a base sequence of SEQ ID NO: 5:

```
SEQ ID NO: 5:
atgaaagtctctgccgcccttctgtgcctgctgctcatagcagccacct tcattcccaagggctcgctcagccagatgcaatcaatgcccagtcac ctgctgttataacttcaccaataggaagatctcagtgcagaggctcgcg agctatagaagaatcaccagcagcaagtgtcccaaagaagctgtgatct tcaagaccattgtggcaaggagatctgtgctgaccccaagcagaagtg ggttcaggattccatggaccacctggacaagcaaacccaaactccgaag acttga
```

(a2) a polynucleotide that has a base sequence obtained by deletion, substitution, insertion, and/or addition of one or more bases in the base sequence of SEQ ID NO: 5 and codes for a protein having a function of the CCL2
(a3) a polynucleotide that has a base sequence with an identity of at least 80% to the base sequence of SEQ ID NO: 5 and codes for a protein having a function of the CCL2
(a4) a polynucleotide that hybridizes to a polynucleotide having a base sequence complementary to the base sequence of SEQ ID NO: 5 under stringent conditions and codes for a polynucleotide having a function of the CCL2
(b1) a polynucleotide having a base sequence of SEQ ID NO: 6:

```
SEQ ID NO: 6:
atgcaggtccctgtcatgcttctgggcctgctgttcacagttgccggct ggagcatccacgtgttggctcagccagatgcagttaacgcccactcac ctgctgctactcattcaccagcaagatgatcccaatgagtaggctggag agctacaagaggatcaccagcagcaggtgtcccaaagaagagtagtttt tgtcaccaagctcaagagagaggtctgtgctgacccccaagaaggaatgg gtccagacatacattaaaaacctggatcggaaccaaatgagatcagaac ctacaactttatttaaaactgcatctgccctaaggtcttcagcacctttt gaatgtgaagttgacccgtaaatctgaagctaatgcatccactacctttt tccacaaccacctcaagcacttctgtaggagtgaccagtgtgacagtga actag
```

(b2) a polynucleotide that has a base sequence obtained by deletion, substitution, insertion, and/or addition of one or more bases in the base sequence of SEQ ID NO: 6 and codes for a protein having a function of the CCL2
(b3) a polynucleotide that has a base sequence with an identity of at least 80% to the base sequence of SEQ ID NO: 6 and codes for a protein having a function of the CCL2
(b4) a polynucleotide that hybridizes to a polynucleotide having a base sequence complementary to the base sequence of SEQ ID NO: 6 under stringent conditions and codes for a polynucleotide having a function of the CCL2

The polynucleotide (a1) is a coding sequence of human CCL2. The base sequence of SEQ ID NO: 5 is the full-length coding sequence (ORF) of the CCL2, and is registered under SWISSPROT Acc. No. P13500, for example.

In the polynucleotide (a2), the number of bases to be subjected to deletion etc. is not particularly limited, and is, for example, one or a few, preferably 1 to 6, more preferably 1 to 4, still more preferably 1 to 3, and particularly preferably 1 or 2.

In the polynucleotide (a3), the identity is not particularly limited, and is, for example, at least 80%, preferably at least 85%, more preferably at least 90%, still more preferably at least 95%, at least 96%, at least 97%, and at least 98%, and particularly preferably at least 99%. The identity can be calculated using BLAST or the like under default conditions, for example (the same applies hereinafter).

In the polynucleotide (a4), the "hybridization under stringent conditions" means hybridization under experimental conditions well known to those skilled in the art, for example. Specifically, the term "stringent conditions" refers to conditions such that a hybrid formed can be identified after carrying out hybridization at 60° C. to 68° C. in the presence of 0.7 to 1 mol/l NaCl and then carrying out washing at 65° C. to 68° C. using a 0.1- to 2-fold SSC solution. Note here that 1×SSC is composed of 150 mmol/l NaCl and 15 mmol/l sodium citrate, for example. In order to select the stringency, for example, the salt concentration and the temperature in the washing step can be optimized as appropriate. Furthermore, it is a common general technical knowledge in the art to add, for example, formamide, SDS, or the like to improve the stringency (hereinafter the same).

The polynucleotide (b1) is a coding sequence of mouse CCL2. The base sequence of SEQ ID NO: 6 is the full-length coding sequence (ORF) of the CCL2, and is registered under SWISSPROT Acc. No. P10148 or NM_011333.3, for example.

In the polynucleotide (b2), the number of bases to be subjected to deletion etc. is not particularly limited, and is, for example, one or a few, preferably 1 to 5, more preferably 1 to 4, still more preferably 1 to 3, and particularly preferably 1 or 2.

In the polynucleotide (b3), the identity is not particularly limited, and is, for example, at least 80%, preferably at least 85%, more preferably at least 90%, still more preferably at least 95%, at least 96%, at least 97%, and at least 98%, and particularly preferably at least 99%.

The vector to which the coding sequence is inserted (hereinafter also is referred to as "base vector") is not particularly limited, and can be set as appropriate depending on the kind of the cell to be transfected with the expression vector, for example. The base vector may be a non-viral vector or a viral vector, for example. Examples of the non-viral vector include plasmid vectors and phage vectors. Examples of the viral vector include retrovirus vectors, DNA virus vectors, and RNA virus vectors. Examples of the retrovirus vectors include lentivirus vectors such as human immunodeficiency virus (HIV) vectors. Examples of the DNA virus vectors include adenovirus vectors, adeno-associated virus vectors (AAV vectors), herpesvirus vectors, vaccinia virus vectors, poxvirus vectors, poliovirus vectors, Sindbis virus vectors, Sendai virus vectors, and SV40. Examples of the RNA virus vectors include lentivirus vectors such as human immunodeficiency virus (HIV) vectors.

The expression vector further may contain a regulatory sequence for regulating the expression of the coding sequence, for example. Examples of the regulatory sequence include: promoters derived from cytomegalovirus (CMV); constitutive promoters such as Rous sarcoma virus (RSV), simian virus-40 (SV-40), musculus β-actin promoters, and herpes simplex virus (HSV); tissue-specific promoters such as thymidine kinase promoters; regulatory promoters such as growth hormone regulatory promoters; promoters that are under the control of the lac operon sequence; and inducible promoters such as a zinc-inducible metallothionein promoter. The regulatory sequence may be arranged according to a known method at a site where the regulatory sequence can regulate the expression of the coding sequence functionally. In addition to the regulatory sequence, the expression vector further may contain an enhancer sequence, a polyadenylation signal, and/or a replication origin sequence (ori), for example.

The expression vector further may contain a coding sequence of a selection marker, for example. Examples of the selection marker include drug-resistant markers, fluorescent protein markers, enzyme markers, and cell surface receptor markers.

The second control agent of the present invention may be a transformant transfected with the expression vector, for example. The host is not particularly limited. The transformant may be, for example, a transformant obtained by transfecting a host other than the undifferentiated cells with the expression vector, or may be transformants obtained by transfecting the undifferentiated cells as a host with the expression vector (i.e., the transformants are the transformed undifferentiated cells).

The former transformant can express the CCL2 or the CCL2-like protein. When the former transformant is used, an undifferentiated state of the undifferentiated cells can be maintained and/or improved by co-culturing the transformant and the undifferentiated cells, for example. Alternatively, for example, by culturing target undifferentiated cells in the presence of the CCL2 or the CCL2-like protein expressed by culturing the transformant, it is possible to maintain and/or improve the undifferentiated state of the undifferentiated cells. The host to be transfected with the expression vector is not particularly limited, and can be set as appropriate depending on the kind of the expression vector, for example.

According to the latter transformants, the CCL2 or the CCL2-like protein can be expressed in the undifferentiated cells. When the latter transformants are used, for example, it is possible to maintain and/or improve the undifferentiated state of the undifferentiated cells by culturing the transformants.

The method for transfecting the host with the expression vector is not particularly limited, and can be set as appropriate depending on the kind of the host, for example. The transfection method may be, for example, a calcium phosphate method, a polyethylene glycol method, a lipofection method using liposome, an electroporation method, a nucleic acid transfection using ultrasonic waves, a transfection using a gene gun, a DEAE-dextran method, a direct injection using a minute glass tube or the like, a hydrodynamic method, a cationic liposome method, and a method using a transfection adjuvant. Examples of the liposome include Lipofectamine and cationic liposome, and examples of the transfection adjuvant include atelocollagen, nano-particles, and polymers.

(2) Second Method for Producing Undifferentiated Cells with Controlled Undifferentiated State The second method for producing undifferentiated cells with their undifferentiated state being controlled according to the present invention is a method using the second control agent. The second production method may be, for example, the one in which the control agent is a transformant obtained by transfecting a host other than the undifferentiated cells with the expression vector, or the one in which the control agent is transformants obtained by transfecting the target undifferentiated cells with the expression vector (i.e., the transformants are the transformed undifferentiated cells), as described above.

In the case where the former transformant is used, the production method of the present invention includes, for example, the step of culturing undifferentiated cells either after or at the same time with the culture of the transformant. As described above, the transformant can express the CCL2 or the CCL2-like protein. Thus, by culturing the undifferentiated cells after or at the same time with the culture of the transformant, the undifferentiated state of the undifferentiated cells can be maintained and/or improved by the expressed CCL2 or CCL2-like protein.

In the present invention, the transformant and the undifferentiated cells preferably are cultured in the same medium.

In the case where the latter transformants are used, the production method of the present invention includes, for example, the step of culturing the transformed undifferentiated cells transfected with the expression vector. As described above, according to the latter transformants, the CCL2 or the CCL2-like protein can be expressed in the undifferentiated cells. Thus, by culturing the transformed undifferentiated cells, the undifferentiated state of the undifferentiated cells can be maintained and/or improved by the expressed CCL2 or CCL2-like protein.

In either of the above cases, the undifferentiated cells are cultured in the presence of the CCL2 and/or the CCL2-like protein provided by the control agent of the present invention, so that it is possible to maintain and/or improve the undifferentiated state of the undifferentiated cells.

As long as the second production method of the present invention includes the above-described culture step, other conditions are not particularly limited, and the above description regarding the step and the conditions in the first production method of the present invention can be referenced, for example.

(3) Second Undifferentiated State-Control Method

A second undifferentiated state-control method according to the present invention is a method for controlling an undifferentiated state of the undifferentiated cells, including the step of culturing the undifferentiated cells according to the second production method of the present invention, thereby maintaining and/or improving the undifferentiated state of the undifferentiated cells.

As long as the control method of the present invention includes the step of culturing the undifferentiated cells according to the second production method of the present invention, other steps and conditions are by no means limited. As to the control method of the present invention, description regarding the first production method, the second production method, and the first undifferentiated state-control method according to the present invention can be referenced, for example.

EXAMPLES

Next, examples of the present invention will be described. It is to be noted, however, that the following examples do not limit the present invention by any means.

(iPS cells)

As mouse iPS cells, iPS-MEF-Ng-20D-17 cells (Takahashi K, Okita K, Nakagawa M, et al., Induction of pluripotent stem cells from fibroblast cultures. Nat Protoc 2007: 2: 3081-3089.) were obtained from the RIKEN BioResource Center, which has a website at www.brc.riken.go.ip, #APS0001.

As human iPS cells, 201B7 cells (Takahashi K et al., Cell (2007) 131, 861-872) were obtained from the RIKEN BioResource Center, which has a website at www.brc.riken.go.ip, HPS0063.

(ES cells)

As mouse ES cells, RF8 cells derived from the 129 SV Jae strain were obtained from the RIKEN BioResource Center, which has a website at www.brc.riken.go.jp.

(Culture Under Feeder Conditions)

Under feeder conditions, the mouse iPS cells or the human iPS cells were cultured on feeder cells SNL76/7 (European Collection of Cell Cultures, ECACC, #07032801) treated with mitomycin C (Sigma-Aldrich Co.). The culture conditions were set to 37° C. and 5% $CO_2$. The medium used was a DMEM (containing glucose at a high concentration and containing no sodium pyruvate) containing 15% FBS, 0.1 mmol/l NEAA, and 0.1 mmol/l 2-Mercaptoethanol.

(Culture Under Feeder Free Conditions)

The medium used was a DMEM (containing glucose at a high concentration and containing no sodium pyruvate) containing 15% FBS, 0.1 mmol/l NEAA, and 0.1 mmol/l 2-Mercaptoethanol, to which LIF (ESGRO, Chemicon) had been added. The LIF was added so that the final concentration thereof in the medium was 1000 units/ml. The mouse iPS cells or human iPS cells were cultured in the medium under the feeder free conditions. The mouse iPS cells were dissociated with 0.25% trypsin and sub-cultured every 2 to 3 days. The human iPS cells were dissociated with an ES/iPS cell dissociation solution and a CTK solution and sub-cultured every 6 to 7 days. The culture conditions were set to 37° C. and 5% $CO_2$.

(Quantitative RT-PCR)

A PrimeScript RT-PCR Kit (trade name, TAKARA BIO INC.), an ABI 7500 Fast real time PCR system (trade name, Applied BioSystems), and a SYBR (registered trademark) Premix Ex Taq (trade name, TAKARA BIO INC.) were used in accordance with their protocols. PCR was carried out by conducting 40 cycles of treatment with a treatment at 94° C. for 5 second and at 62.5° C. for 20 seconds as 1 cycle. The expression level of each gene was calculated by normalizing the relative amount of mRNA in the gene to Gapdh mRNA according to the $2^{-\Delta\Delta c_T}$ method (Thomse R, Solvsten C A, Linnet T E, et al., Analysis of qPCR data by converting exponentially related Ct values into linearly related X0 values. J Bioinform Comput Biol 2010: 8: 885-900.).

(Primers)

The following primers were used in the quantitative RT-PCR etc. of the undifferentiated marker genes. In the following, "F" stands for "forward primer", and "R" stands for "reverse primer".

```
m-Gapdh_F
                                        (SEQ ID NO: 9)
gaagcccatcaccatcttcc m-Gapdh_R
                                       (SEQ ID NO: 10)
gatgacccttttggctccac m-c-Myc_F
                                       (SEQ ID NO: 11)
tagtgctgcatgaggagacacc m-c-Myc_R
                                       (SEQ ID NO: 12)
tttgcctcttctccacagacac m-Dax1_F
                                       (SEQ ID NO: 13)
tatctgaaagggaccgtgctc m-Dax1_R
                                       (SEQ ID NO: 14)
atccggatgtgctcagtaagg m-Klf4_F
                                       (SEQ ID NO: 15)
ctttcctgccagaccagatg m-Klf4_R
                                       (SEQ ID NO: 16)
ttcttcccctctttggcttg m-Nanog 1 F
                                       (SEQ ID NO: 17)
aagtactcagcctccagca m-Nanog 1 R
                                       (SEQ ID NO: 18)
gtgctgagcccttctgaatc m-Oct3/4_F
                                       (SEQ ID NO: 19)
agtttgccaagctgctgaag m-Oct3/4_R
                                       (SEQ ID NO: 20)
tcttaaggctgagctgcaagg m-Sox2_F
                                       (SEQ ID NO: 21)
tgaacgccttcatggtatgg m-Sox2_R
                                       (SEQ ID NO: 22)
ttgtgcatcttggggttctc m-Utf1_F
                                       (SEQ ID NO: 23)
agtcgttgaataccgcgttg m-Utf1_R
                                       (SEQ ID NO: 24)
agaaacggtttggtcgaagg m-Tbx3 1 F
                                       (SEQ ID NO: 25)
cagctcacactgcagtccat m-Tbx3 1 R
                                       (SEQ ID NO: 26)
tggagacagcaggagaggat Cxcl1 F
                                       (SEQ ID NO: 27)
gctgggattcacctcaagaa Cxcl1 R
                                       (SEQ ID NO: 28)
aagggagcttcagggtcaag Dcn F
                                       (SEQ ID NO: 29)
tctccaggaacttcgtgtcc Dcn R
                                       (SEQ ID NO: 30)
ctccgttttcaatcccagag Ccl2 F
                                       (SEQ ID NO: 31)
cccaatgagtaggctggaga Ccl2_R
                                       (SEQ ID NO: 32)
tctggacccattccttcttg Btc F
                                       (SEQ ID NO: 33)
gcacaggtaccacccctaga Btc R
                                       (SEQ ID NO: 34)
gccccaaagtagcctttctc Gsto2 F
                                       (SEQ ID NO: 35)
gtaaggtcccgcctttaagc
```

-continued

Gsto2 R  
cgccgaagaaggtagtgttc (SEQ ID NO: 36)

Mmp13 F  
gccctgatgtttcccatcta (SEQ ID NO: 37)

Mmp13 R  
tttttgggatgcttagggttg (SEQ ID NO: 38)

EG545886 F  
acccaggtctcaggttcaga (SEQ ID NO: 39)

EG545886 R  
tgctgttgctgttcctgttc (SEQ ID NO: 40)

Ltbp3 F  
ctgcttccaggacacattgc (SEQ ID NO: 41)

Ltbp3 R  
tgtgggcacttgtgacactt (SEQ ID NO: 42)

Ltbp1 F  
ggaagtttcctgtgtgtctgc (SEQ ID NO: 43)

Ltbp1 R  
cggccatccctacacatatc (SEQ ID NO: 44)

Areg F  
catgcactgccaagtttcag (SEQ ID NO: 45)

Areg R  
ccacaccgttcaccaaagta (SEQ ID NO: 46)

Ecm1 F  
ggagactccgagttgaccac (SEQ ID NO: 47)

Ecm1 R  
ggccagtcttcctcgtacac (SEQ ID NO: 48)

Ccl19 F  
cagtctgaaggcacagcaag (SEQ ID NO: 49)

Ccl19 R  
ccactggtgggaaaataacc (SEQ ID NO: 50)

Ccl17 F  
tgtccctgggaagctgttat (SEQ ID NO: 51)

Ccl17 R  
ctttggagttggggttttca (SEQ ID NO: 52)

Plau F  
gcctgctgtccttcagaaac (SEQ ID NO: 53)

Plau R  
caaactgccttaggccaatc (SEQ ID NO: 54)

Msln F  
agcacaatgtgagcatggac (SEQ ID NO: 55)

Msln R  
acggacagggcttttatcct (SEQ ID NO: 56)

Traf1 F  
gatggctcaggcaagaagac (SEQ ID NO: 57)

Traf1 R  
agcatgctctcggttgttct (SEQ ID NO: 58)

Cav1 F  
gcacaccaaggagattgacc (SEQ ID NO: 59)

Cav1 R  
tcccttctggttctgcaatc (SEQ ID NO: 60)

Lhfp F  
tcggaactcatctccaggac (SEQ ID NO: 61)

Lhfp R  
gccagagatgtagccacaag (SEQ ID NO: 62)

D12ertd647e F  
tattgctaatgggggtggag (SEQ ID NO: 63)

D12ertd647e R  
cagagcccacgatgacagta (SEQ ID NO: 64)

Col4a5 F  
gggggaaccaggcagtataa (SEQ ID NO: 65)

Col4a5 R  
taaacctggtggtcctggag (SEQ ID NO: 66)

Igfbp7 F  
ggaaaatctggccattcaga (SEQ ID NO: 67)

Igfbp7 R  
tgcgtggcactcatactctc (SEQ ID NO: 68)

Ltbp2 F  
agggagcagacagagcagag (SEQ ID NO: 69)

Ltbp2 R  
ctttgtcagggagggtctca (SEQ ID NO: 70)

Serpina3g F  
cattgatggtgctggtgaac (SEQ ID NO: 71)

Serpina3g R  
tcatggacacaatcacagacc (SEQ ID NO: 72)

Ppbp F  
gcgctgcagatgtacgaata (SEQ ID NO: 73)

Ppbp R  
ccattcttcagtgtggctata (SEQ ID NO: 74)

S100a4 F  
ttgtgtccaccttccacaaa (SEQ ID NO: 75)

-continued

S100a4 R
(SEQ ID NO: 76)
tggaatgcagcttcatctgt

Serpinb2 F
(SEQ ID NO: 77)
caccacaggggggattatttg

Serpinb2 R
(SEQ ID NO: 78)
aggaagtccactgcttctgg

Tcn F
(SEQ ID NO: 79)
accagacatccaccaccatt

Tcn R
(SEQ ID NO: 80)
tcaggtgcaggcaaatagg

Gm566 (Bcl2l15) F
(SEQ ID NO: 81)
cagatgaaccatgctcagga

Gm566 (Bcl2l15) R
(SEQ ID NO: 82)
ctgtcctccaatggttaccg m-Zfp42_F
(SEQ ID NO: 83)
acgagtggcagtttcttcttggga m-Zfp42_R
(SEQ ID NO: 84)
tatgactcacttccaggggggcact m-Cripto_F
(SEQ ID NO: 85)
atggacgcaactgtgaacatgatgttcgca m-Cripto_R
(SEQ ID NO: 86)
ctttgaggtcctggtccatcacgtgaccat m-Ecat1_F
(SEQ ID NO: 87)
tgtgggggccctgaaaggcgagctgagat m-Ecat1_R
(SEQ ID NO: 88)
atgggccgccatacgacgacgctcaact m-Esg1_F
(SEQ ID NO: 89)
gaagtctggttccttggcaggatg m-Esg1_R
(SEQ ID NO: 90)
actcgatacactggcctagc m-Eras_F
(SEQ ID NO: 91)
actgccctcatcagactgctact m-Eras_R
(SEQ ID NO: 92)
cactgccttgtactcgggtagctg m-Fgf4_F
(SEQ ID NO: 93)
cgtggtgagcatcttcggagtgg m-Fgf4_R
(SEQ ID NO: 94)
ccttcttggtccgcccgttctta Example 1

In the present example, a CCL2 protein was overexpressed in the mouse iPS cells, and the effect thereof on the expression of undifferentiated marker genes was examined.

(1) Effect of Overexpression of CCL2 on Expression of Undifferentiated Marker Genes In the following manner, CCL2 was overexpressed in the mouse iPS cells, and the expression levels of undifferentiated marker genes were examined. The undifferentiated marker genes were the Ecat1 gene, Cripto gene, Oct3/4 gene, Zfp42 gene, Esg1 gene, Eras gene, Fgf4 gene, Dax1 gene, Nanog gene, Sox2 gene, Klf4 gene, cMyc gene, Tbx3 gene, and Eed gene.

A Ccl2 expression vector that overexpresses CCL2 was constructed. The CCL2 to be expressed was a mouse-derived protein having a full-length amino acid sequence of SEQ ID NO: 3. First, using a Gateway Technology (Invitrogen), a full-length cDNA (SEQ ID NO: 6) coding for the CCL2 was cloned into a pENTER/D-TOPO vector. The cloned sequence was confirmed, and thereafter, the full-length cDNA was inserted into an EF-α1 promoter-containing pEF-DEST51 vector (Invitrogen) using a Gateway LR Clonase II Enzyme Mix (Invitrogen), thus constructing the Ccl2 expression vector. The Ccl2 expression vector was purified using an Endotoxin free Plasmid maxi prep kit (Qiagen) in accordance with its protocol.

(NP_035463.1) 148 aa
SEQ ID NO: 3
MQVPVMLLGLLFTVAGWSIHVLAQPDAVNAPLTCCYSFTSKMIPMSRLES

YKRITSSRCPKEAVVFVTKLKREVCADPKKEWVQTYIKNLDRNQMRSEPT

TLFKTASALRSSAPLNVKLTRKSEANASTTFSTTTSSTSVGVTSVTVN (NM_011333.3) 447 nt
SEQ ID NO: 6
ATGCAGGTCCCTGTCATGCTTCTGGGCCTGCTGTTCACAGTTGCCGGCT

GGAGCATCCACGTGTTGGCTCAGCCAGATGCAGTTAACGCCCCACTCAC

CTGCTGCTACTCATTCACCAGCAAGATGATCCCAATGAGTAGGCTGGAG

AGCTACAAGAGGATCACCAGCAGCAGGTGTCCCAAAGAAGCTGTAGTTT

TTGTCACCAAGCTCAAGAGAGAGGTCTGTGCTGACCCCAAGAAGGAATG

GGTCCAGACATACATTAAAAACCTGGATCGGAACCAAATGAGATCAGAA

CCTACAACTTTATTTAAAACTGCATCTGCCCTAAGGTCTTCAGCACCTTT

GAATGTGAAGTTGACCCGTAAATCTGAAGCTAATGCATCCACTACCTTTT

CCACAACCACCTCAAGCACTTCTGTAGGAGTGACCAGTGTGACAGTGAA

CTAG

Next, the mouse iPS cells cultured under the feeder free conditions were seeded in a 12-well dish at a density of $3 \times 10^5$ cells/well. The amount of a medium to be added to the dish was set to 1 ml/well. Then, using 16 μl of a Lipofectamine 2000 (Invitrogen) and 4.8 μg of the Ccl2 expression vector per well, the mouse iPS cells were transfected with the Ccl2 expression vector. These mouse iPS cells were cultured for another 24 hours under feeder free conditions. Thereafter, total RNAs were extracted, and the expression levels of the undifferentiated marker genes were examined. The expressions of the undifferentiated marker genes were examined by the quantitative RT-PCR using the above-described primers. Furthermore, as a negative control, the expression levels of the undifferentiated marker genes also were examined with regard to the mouse iPS cells cultured in the same manner as in the above except that they were not transfected with the expression vector. Then, the fold changes in expression level relative to the negative control were calculated.

The results are shown in FIG. 1. FIG. 1 is a graph showing the fold changes in expression of the undifferentiated marker genes in the mouse iPS cells in which the CCL2 was overexpressed. The vertical axis indicates the fold change (-fold), and the horizontal axis indicates the examined undifferentiated marker genes.

As can be seen from FIG. 1, by overexpressing the CCL2 in the mouse iPS cells, the expressions of the undifferentiated marker genes, namely, the Nanog gene, the Sox2 gene, the Klf4 gene, and the Tbx3 gene, were increased markedly.

(2) Effect of Ccl2 Gene Knockdown on Expression of Undifferentiated Marker Genes Ccl2 gene knockdown was caused in the mouse iPS cells and the expression levels of undifferentiated marker genes were determined, as specifically described in the following. The undifferentiated marker genes were the Klf4 gene and the Tbx3 gene.

The knockdown of the Ccl2 gene was achieved in the following manner with the use of Stealth siRNA (Invitrogen). First, the mouse iPS cells cultured under the feeder free conditions were seeded in a 12-well dish at a density of 6×10$^4$ cells/well. The amount of a medium to be added to the dish was set to 1 ml/well. After culturing the mouse iPS cells for 24 hours, 16 µl of a Lipofectamine 2000 (Invitrogen) per well and Stealth siRNA (trade name: CCL2 Stealth RNAi (registered trademark) siRNA, Invitrogen) were added, and the mouse iPS cells were transfected with the Stealth siRNA in accordance with its protocol. The sequence of siRNA against the Ccl2 gene in the Stealth siRNA was as shown in SEQ ID NO: 7:

```
                                         (SEQ ID NO: 7)
CAUUCACCAGCAAGAUGAUCCCAAU
```

The Stealth siRNA was added so that the final concentration thereof per well was 20 µmol/l. Then, 24 hours after the transfection, total RNAs were extracted, and the expression levels of the undifferentiated marker genes and the Ccl2 gene in the mouse iPS cells were determined by the quantitative RT-PCR.

Also, as a negative control, the mouse iPS cells were subjected to transfection in the same manner as in the above, except that Stealth siRNA (trade name: Stealth RNAi (registered trademark) Negative Control Medium GC, Duplex-catalog number 12935-300, Invitrogen) was used, and the expressions of the undifferentiated marker genes were measured (n=3). Then, the fold changes in expression level relative to the negative control were calculated.

Figure 2:
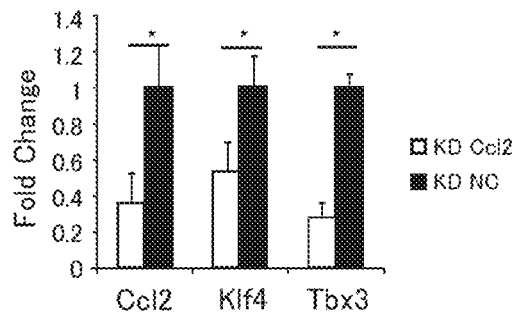
FIG. 2 is a graph showing the fold changes in expression of the Ccl2 gene and the undifferentiated marker genes in mouse iPS cells in which the Ccl2 gene had been knocked down in the example of the present invention.

The results are shown in FIG. 2. FIG. 2 is a graph showing the fold changes in expression of the Ccl2 gene and the undifferentiated marker genes in the mouse iPS cells in which the Ccl2 gene had been knocked down. The vertical axis indicates the fold change (-fold) in expression level relative to the negative control, and the horizontal axis indicates the Ccl2 gene and the undifferentiated marker genes. Regarding each of the genes, the open bar shows the result obtained in the mouse iPS cells in which the Ccl2 gene had been knocked down, and the solid bar shows the result obtained in the mouse iPS cells in which the Ccl2 gene had not been knocked down (control).

As can be seen from FIG. 2, by the knockdown of the Ccl2 gene, the expressions of the undifferentiated marker genes were decreased markedly.

Example 2

In the present example, the mouse iPS cells were cultured in the presence of CCL2 under feeder free conditions, and the improvement in undifferentiation potency by CCL2 was examined.

(1) Improvement in Undifferentiation Potency by Addition of CCL2

In the present example, the above-described DMEM to which the LIF and mouse recombinant CCL2 (MCP-1, #479-JE-010, R&D Systems) had been added was used. In the medium, the final concentration of the LIF was set to 25 units/ml, and the concentration of the recombinant CCL2 was set to 500 ng/ml. The amount of the medium to be added to a 12-well dish was set to 1 ml per well. On the other hand, in a comparative example, the above-described DMEM containing the LIF but not containing the CCL2 was used. The final concentration of the LIF was set to 25 units/ml.

The mouse iPS cells cultured under feeder free conditions were cultured in the medium of the example and the medium of the comparative example, respectively. The mouse iPS cells were seeded in the 12-well dish at a density of 6×10$^4$ cells/well. 24 hours after the culture, as a cell population exhibiting pluripotency, a Nanog-GFP positive cell population was observed by flow cytometry analysis.

The flow cytometry analysis was carried out in the following manner. After the mouse iPS cells had been cultured in the above described manner, the cells were collected from the wells, and were suspended again in an ES medium containing 25 units/ml of LIF. As the ES medium, a DMEM (containing glucose at a high concentration and containing no sodium pyruvate) containing 15% FBS, 0.1 mmol/l NEAA, and 0.1 mmol/l 2-Mercaptoethanol was used. Then, this cell suspension was applied to a flow cytometer (trade name: BD FAC-SAria (registered trademark) II, Becton, Dickinson and Company), and analyzed in accordance with the protocol of the flow cytometer. At this time, as a cell population having pluripotency, i.e., undifferentiated cell population, a Nanog-GFP-positive region sorted out based on FITC-A>10$^4$ was monitored. The raw data was analyzed by a program (FlowJo, ver. 7), and plotted in the form of density plot. The iPS cells were produced from MEF of a modified mouse with a GFP protein being incorporated in the promoter region of the Nanog gene. Thus, when the cells expressed the Nanog gene, it means the cells were Nanog-GFP positive, so that the GFP was produced and this GFP was detected by the FACS.

Figures 3A, 3B:
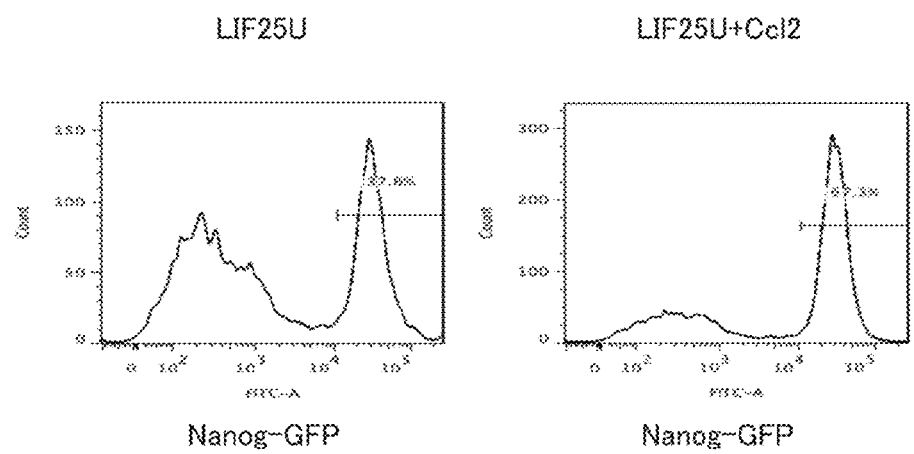
FIG. 3 shows graphs showing the results of the flow cytometry analysis with respect to mouse iPS cells expressing the Nanog gene as an undifferentiated marker gene in another example of the present invention.

The results are shown in FIG. 3. FIG. 3 shows graphs showing the results of the flow cytometry analysis. FIG. 3A shows the results obtained when the medium of the comparative example was used, and FIG. 3B shows the results obtained when the medium of the example was used. In FIG. 3, the vertical axis indicates the number of cells.

As can be seen from FIG. 3A, when the cells were cultured in the medium of the comparative example, the proportion of the Nanog-GFP positive mouse iPS cells was 37.6%. In contrast, when the cells were cultured in the medium of the example, the proportion of the Nanog-GFP positive mouse iPS cells was increased to 67.3% by the addition of the recombinant CCL2. From these results, it was found that, by the addition of the recombinant CCL2, the differentiation of the mouse iPS cells was inhibited, in other words, the undifferentiation potency of the mouse iPS cells was improved.

(2) Effect of CCL2 on LIF Concentration

The mouse iPS cells were cultured and the flow cytometry analysis was performed in the same manner as in the above item (1), except that the concentration of the LIF in the media of the example and the comparative example in the above item (1) was set to 25, 50, 100, 500, and 1000 units/ml.

Figure 4:
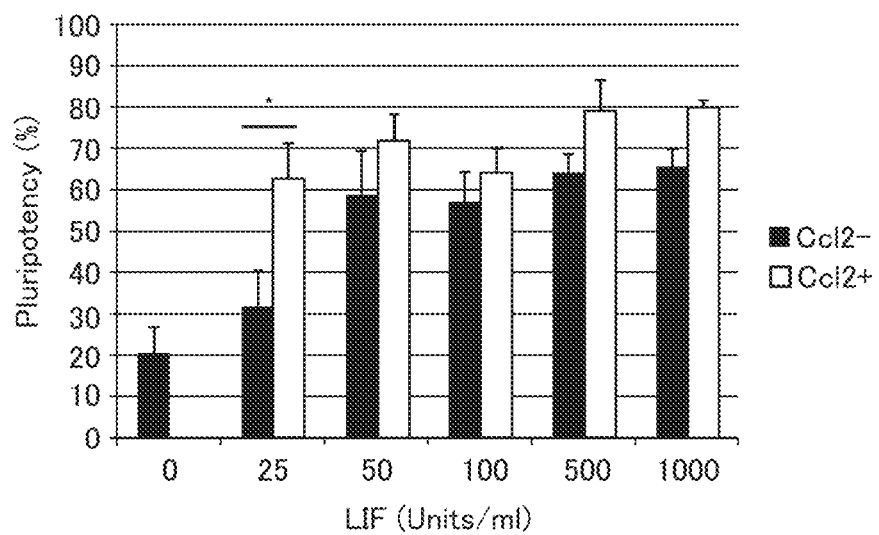
FIG. 4 is a graph showing the results of the flow cytometry analysis with respect to the mouse iPS cells expressing the Nanog gene as an undifferentiated marker gene in the example of the present invention.

The results are shown in FIG. 4. FIG. 4 is a graph showing the results of the FACS analysis. In FIG. 4, the vertical axis indicates the proportion (%) of the Nanog-GFP positive mouse iPS cells in all the cells. The open bars show the results obtained in the example where the CCL2 was added, and the solid bars show the results obtained regarding the comparative example where the CCL2 was not added.

As can be seen from FIG. 4, by further adding the CCL2, the differentiation was inhibited and the proportion of the Nanog-GFP positive mouse iPS cells was increased regardless of the concentration of the LIF. From these results, it can be seen that, by the addition of the CCL2, the differentiation of the mouse iPS cells was inhibited further, in other words, the undifferentiation potency was improved further.

Example 3

In the present example, the mechanism by which the CCL2 promotes the Klf4 gene expression was analyzed.

The promotion of phosphorylation of STAT3 protein on the Jak/Stat3 pathway by overexpression of the CCL2 was examined.

The mouse iPS cells transfected with the Ccl2 expression vector were cultured for 24 hours in the same manner as in Example 1. After the culture, the mouse iPS cells were washed with PBS, and then were suspended in 100 μl of a mammalian m-PER lysis buffer. The suspension was passed through a 26-gauge needle for 10 minutes to homogenize the cells. Then, the suspension was centrifuged at 13,000 rpm and 4° C. for 5 minutes, and the supernatant was collected. The protein concentration in the supernatant was measured using a Pierce (registered trademark) BCA Protein assay (trade name, Thermo Scientific). Next, the supernatant was subjected to Western blotting to detect a target protein. Specifically, first, the supernatant (total protein: 10 μg) was applied to a Novex Gel electrophoresis system with 4%-12% Bis-Tris gels, and was blotted on a nitrocellulose membrane. Then, the membrane was incubated with a primary antibody against the target protein. After washing the membrane, the membrane was incubated with a labeled secondary antibody labeled with horseradish peroxidase, and a color-developing reaction was caused using a coloring reagent (trade name: ECL plus, GE Healthcare). Then, luminescence on the membrane was detected using a Fuji LAS-3000 luminescent image analyzer.

As the primary antibody, an anti-phosphorylated STAT3 antibody (anti-pSTAT3 antibody, commercially available from CST, #9145) was used for the phosphorylated STAT3 (pSTAT3), an anti-STAT3 antibody (CST, #9132) was used for the STAT3 protein, and an anti-GAPDH antibody (Santa Cruz Biotechnology Inc, #25778) was used for GAPDH, which is an expression control. As an antibody used in the labeled secondary antibody, an anti-rabbit IgG (Cell Signaling, anti-rabbit IgG HPR-linked antibody (#7074)) or an anti-mouse IgG (Cell Signaling, anti-mouse IgG HPR-linked antibody (#7076)) was used depending on the kind of the primary antibody. The anti-phosphorylated STAT3 antibody was stripped from the membrane by incubating the membrane at room temperature for 15 minutes using a stripping reagent (trade name: 1×ReBlot (registered trademark) Plus Strong Antibody Stripping Solution, Millipore). Then, the ratio of the phosphorylated STAT3 to the non-phosphorylated STAT3 (pSTAT3/STAT3) was determined.

Furthermore, as a negative control, the mouse iPS cells were cultured and subjected to Western blotting in the same manner as in the above, except that the mouse iPS cells were not transfected with the Ccl2 expression vector. Then, assuming that the value of pSTAT3/STAT3 in the negative control was "1", the relative value was calculated.

Figures 5A, 5B:
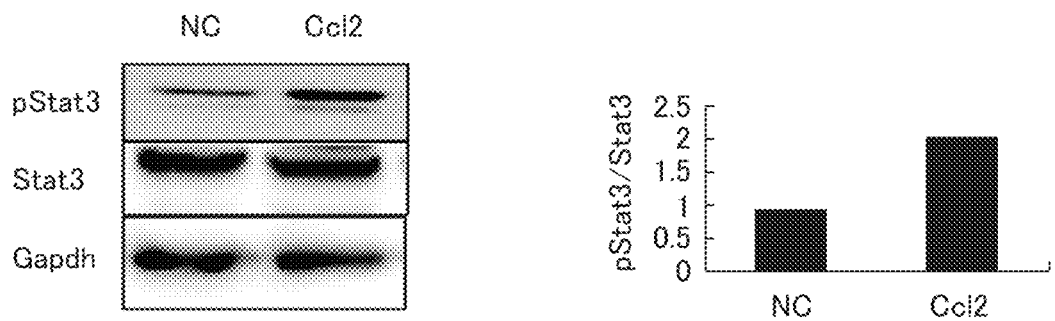
FIG. 5A shows photographs showing the results of Western blotting.
FIG. 5B is a graph showing the ratio of phosphorylated STAT3 to non-phosphorylated STAT3.

The results are shown in FIG. 5. The photographs of FIG. 5A show the results of the Western blotting. In FIG. 5A, "NC" indicates the results obtained regarding the negative control, and "Ccl2" indicates the results obtained regarding the mouse iPS cells transfected with the Ccl2 expression vector. FIG. 5B is a graph showing the relative value of the ratio of the phosphorylated STAT3 to the non-phosphorylated STAT3 (pSTAT3/STAT3).

As can be seen from FIGS. 5A and 5B, owing to the overexpression of the CCL2, the ratio of the phosphorylated pSTAT3 increased relative to the non-phosphorylated STAT3. That is, it was found that the overexpression of the CCL2 promoted the phosphorylation of STAT3. From these results, it is speculated that CCL2 promotes the expression of the Klf4 gene through phosphorylation of STAT3.

Example 4

In the present example, the mechanism by which the CCL2 promotes the Tbx3 gene expression was analyzed. In the item (2) of Example 1, it was confirmed that the CCL2 promotes not only the expression of the Klf4 gene but also the expression of the Tbx3 gene. Thus, the possibility that the promotion of the expression of the Klf4 gene by CCL2 may directly control the expression of the Tbx3 gene was examined.

(1) Effect of CCL2 on Phosphorylation in PI3K Pathway and MAPK Pathway

It has been reported that the expression of the Tbx3 gene is promoted either through phosphorylation of AKT by the activation of the PI3K pathway or through inhibition of the MAPK pathway. Thus, the promotion of phosphorylation of AKT in the PI3K pathway and the promotion of phosphorylation of ERK1/2 in the MAPK pathway by CCL2 were examined.

The mouse iPS cells transfected with the Ccl2 expression vector were cultured and subjected to Western blotting to detect a target protein in the same manner as in the item (2) of Example 3. As the primary antibody, an anti-pAKT antibody (CST, #9272) was used for phosphorylated AKT (pAKT), an anti-AKT antibody (CST, #9271) was used for non-phosphorylated AKT, an anti-pERK1/2 antibody (Promega, #V8031) was used for phosphorylated ERK1/2 (pERK1/2), and an anti-ERK1/2 antibody (CST, #9102) was used for ERK1/2. The Western blotting was carried out in the same manner as in the item (2) of Example 3, except that these primary antibodies were used.

Figures 6A, 6B:
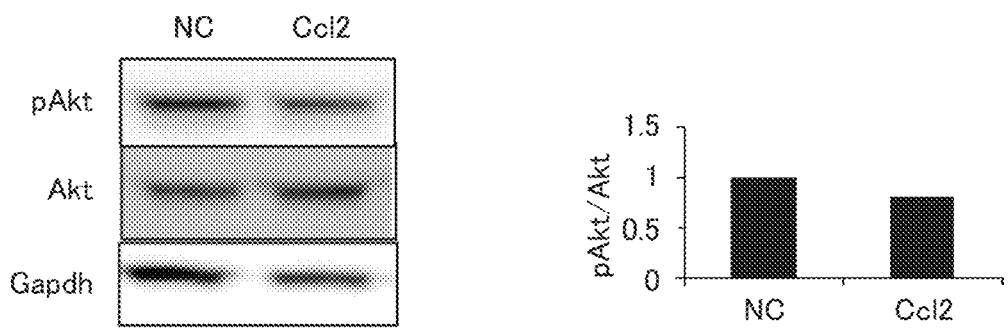
FIG. 6A shows photographs showing the results of Western blotting.
FIG. 6B is a graph showing the ratio of phosphorylated AKT to non-phosphorylated AKT.

The results are shown in FIGS. 6 and 7. FIG. 6 shows the results regarding the effect on the phosphorylation of AKT, and FIG. 7 shows the results regarding the effect on the phosphorylation of ERK1/2. The photographs of each of FIGS. 6A and 7A show the results of the Western blotting. In FIGS. 6A and 7A, "NC" indicates the results obtained regarding the negative control, and "Ccl2" indicates the results obtained regarding the mouse iPS cells transfected with the Ccl2 expression vector. The graph of each of FIGS. 6B and 7B shows the ratio of the phosphorylated protein to the non-phosphorylated protein (pAKT/AKT or pERK1/2/ERK1/2).

As can be seen from FIGS. 6A and 6B, even though the CCL2 was overexpressed, the phosphorylation of AKT and ERK1/2 was not promoted. It can be said that this suggests that phosphorylation of AKT and phosphorylation of ERK1/2 are not involved in the inhibition of the differentiation by CCL2. From these results, it is interpreted that the PI3K pathway and the MAPK pathway are not involved in the improvement of the undifferentiation potency by CCL2.

(2) Effect of CCL2 on PI3K Pathway

In the above item (1), it was suggested that the PI3K pathway is not involved in the improvement in the undifferentiation potency by CCL2. Thus, the effect of CCL2 on the undifferentiation potency in the case where the PI3K pathway is inhibited was examined.

The medium of a negative control used was the above-described DMEM containing the above-described LIF. In the medium, the final concentration of the LIF was set to 25 units/ml. The medium used for a comparative example was the above-described DMEM containing the above-described LIF and LY294002 (Promega KK) as a PI3K inhibitor. In the medium, the final concentration of the LIF was set to 25 units/ml, and the concentration of the inhibitor was set to 5 ng/ml. The media used for the present example were: the above-described DMEM containing the above-described LIF and the above-described recombinant CCL2; and the above-described DMEM containing the LIF, the recombinant CCL2, and the PI3K inhibitor. In these media, the final concentration of the LIF was set to 25 units/ml, the concentration of the recombinant CCL2 was set to 500 ng/ml, and the concentration of the inhibitor was set to 5 ng/ml.

The mouse iPS cells were cultured and subjected to flow cytometry analysis in the same manner as in the item (2) of Example 2, except that these media were used. The results are shown in FIG. 8. FIG. 8 is a graph showing the results of the flow cytometry analysis, and the vertical axis indicates the proportion (%) of Nanog-GFP positive-mouse iPS cells in all the cells.

As can be seen from the result of the comparative example shown in FIG. 8, when the PI3K inhibitor was added to the medium (without the CCL2), the number of undifferentiated cells having pluripotency decreased markedly. This demonstrates that, in the absence of CCL2, the activation of the PI3K pathway is essential for the maintenance of the undifferentiation potency of undifferentiated cells. However, as can be seen from the result of the example shown in FIG. 8, it was found that, when the recombinant CCL2 was further added to the medium, not only that the decrease in the number of cells caused by the PI3K inhibitor was obviated, but also that further increase in the number of cells was observed.

Furthermore, after the culture of the mouse iPS cells, the expression level of the Tbx3 gene was determined in the same manner as in the item (1) of Example 1. Then, the fold change in expression level relative to the negative control was calculated. The results are shown in FIG. 9. FIG. 9 is a graph showing the fold change in the expression level of the Tbx3 gene. The vertical axis indicates the fold change (-fold). As can be seen from the result of the comparative example shown in FIG. 9, when the PI3K inhibitor was added to the medium, the expression level of the Tbx3 gene decreased markedly. However, as can be seen from the result of the example shown in FIG. 9, it was found that, when the recombinant CCL2 further was added to the medium, not only that the decrease in expression level of the Tbx3 gene caused by the PI3K inhibitor was obviated, but also that further increase in the expression level of the Tbx3 gene was observed.

(3) Effect of Klf4 Gene Knockdown on Tbx3 Gene Expression

The results obtained in the above items (1) and (2) suggest that the expression of the Tbx3 gene is promoted through the promotion of the expression of the Klf4 gene by CCL2. Thus, the effect of the knockdown of the Klf4 gene on the expression of the Tbx3 gene was examined.

The knockdown of the Klf4 gene was achieved according to the knockdown method described in the item (2) of Example 1, except that a product with a trade name "CCL2 Stealth RNAi (registered trademark) siRNA" (Invitrogen Corporation) was used as the Stealth siRNA (Invitrogen Corporation). The sequence of siRNA against the Klf4 gene in the Stealth siRNA was as shown in SEQ ID NO: 8.

(SEQ ID NO: 8)
CAAGUUUGUGCUGAAGGCGUCUCUG

Then, in the same manner as in the item (2) of Example 1, the mouse iPS cells were transfected with the Stealth siRNA, total RNAs were extracted 24 hours after the culture, and the expression level of the Tbx3 gene in the mouse iPS cells was determined by quantitative RT-PCR.

Figure 10:
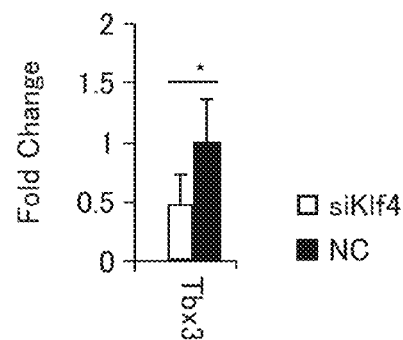
FIG. 10 is a graph showing the fold change in expression of the Tbx3 gene in mouse iPS cells in which the Klf4 gene had been knocked down in the example of the present invention.

The results are shown in FIG. 10. FIG. 10 is a graph showing the fold change in the expression of the Tbx3 gene in the mouse iPS cells in which the Klf4 gene had been knocked down. The vertical axis indicates the fold change (-fold) relative to the negative control, and the horizontal axis indicates the Tbx3 gene. As to the results obtained regarding the Tbx3 gene, the open bar shows the result obtained in the mouse iPS cells in which the Klf4 gene had been knocked down, and the solid bar shows the result obtained in the mouse iPS cells in which the Klf4 gene had not been knocked down (control).

As can be seen from FIG. 10, it was found that, as a result of the knockdown of the Klf4 gene, the expression of the Tbx3 gene decreased markedly.

Also, from the data regarding Klf4 ChIP stored in a database (MPromDB), it was confirmed that the Klf4 gene binds to the promoter region of the Tbx3 gene.

Figure 11:
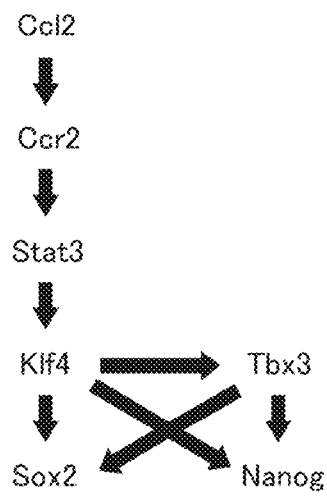
FIG. 11 illustrates a putative undifferentiated state-maintaining or -improving mechanism in which CCL2 is involved.

The above results suggest that CCL2 promotes the phosphorylation of STAT3, which promotes the expression of the Klf4 gene, and also suggests that the promotion of the Klf4 gene expression leads to the promotion of the Tbx3 gene expression. Based on these results, it is interpreted that a pathway shown in FIG. 11 newly is promoted by CCL2, which allows the undifferentiated state of undifferentiated cells to be maintained (differentiation is inhibited). It is to be noted, however, that the present invention is by no means limited by these putative mechanisms.

Example 5

In the present example, the CCL2 was overexpressed in mouse ES cells, and the effect thereof on the expression of the undifferentiated marker genes was examined.

The CCL2 was overexpressed and the expressions of the undifferentiated marker genes were measured in the same manner as in the item (1) of Example 1, except that the ES cells were used instead of the mouse iPS cells. Furthermore, as a negative control, the expression levels of the undifferentiated marker genes were determined in the same manner regarding the mouse ES cells cultured in the same manner except that they had not been transfected with the Ccl2 expression vector. Then, the fold changes in the expression level relative to the negative control were calculated.

Figure 12:
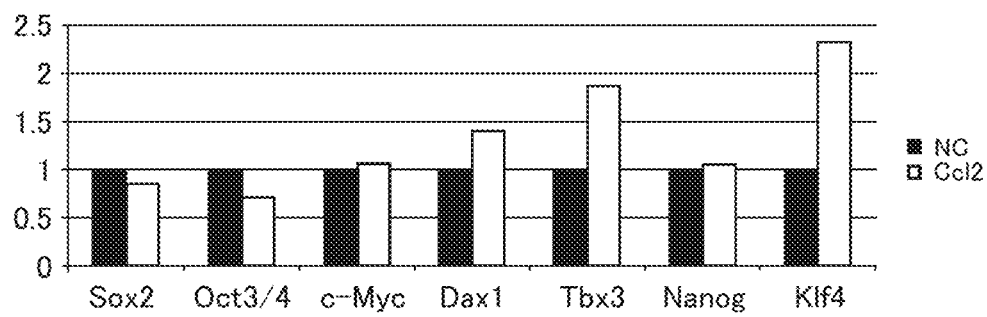
FIG. 12 is a graph showing the fold changes in expression of undifferentiated marker genes in mouse ES cells in which CCL2 was overexpressed in still another example of the present invention.

The results are shown in FIG. 12. FIG. 12 is a graph showing the fold changes in expression of the undifferentiated marker genes in the mouse ES cells in which the CCL2 was overexpressed. The vertical axis indicates the fold change (-fold), and the horizontal axis indicates the examined undifferentiated marker genes. Regarding each of the undifferentiated marker genes, the open bar shows the result obtained in the mouse ES cells in which the CCL2 was overexpressed, and the solid bar shows the result obtained in the negative control. In the former case (open bar), the concentration of the LIF in the medium was 1000 units/ml and the concentration of the CCL2 in the medium was 500 ng/ml. In the latter case (solid bar), the concentration of the LIF in the medium was 1000 units/ml and the concentration of the CCL2 in the medium was 0 ng/ml.

As can be seen from FIG. 12, as in the case of the mouse iPS cells in Example 1, by the addition of the CCL2, the expressions of the Klf4 gene and the Tbx3 gene, which are both undifferentiated marker genes, increased markedly. This result demonstrates that CCL2 also can improve the undifferentiation potency of mouse ES cells.

Example 6

In the present example, the CCL2 was added to the mouse iPS cells under the feeder free conditions, and the effect of the CCL2 on the expressions of the undifferentiated marker genes was examined.

In the present example, the above-described DMEM not containing LIF but containing the above-described recombinant CCL2 was used. In the medium, the concentration of the recombinant CCL2 was set to 2500 ng/ml. In a comparative example, the above-described DMEM not containing the recombinant CCL2 but containing the LIF was used. In the medium, the final concentration of the LIF was set to 1000 units/ml. The amount of the medium to be added to a 12-well dish was set to 1 ml per well.

The mouse iPS cells cultured under the feeder free conditions were cultured in the medium of the example and the medium of the comparative example, respectively. The mouse iPS cells were seeded in the 12-well dish at a density of $6 \times 10^4$ cells/well. 24 hours after the culture, the expression levels of the undifferentiated marker genes were determined in the same manner as in the item (1) of Example 1. Then, the fold changes in expression level relative to the results obtained when the LIF was added were calculated.

Figure 13:
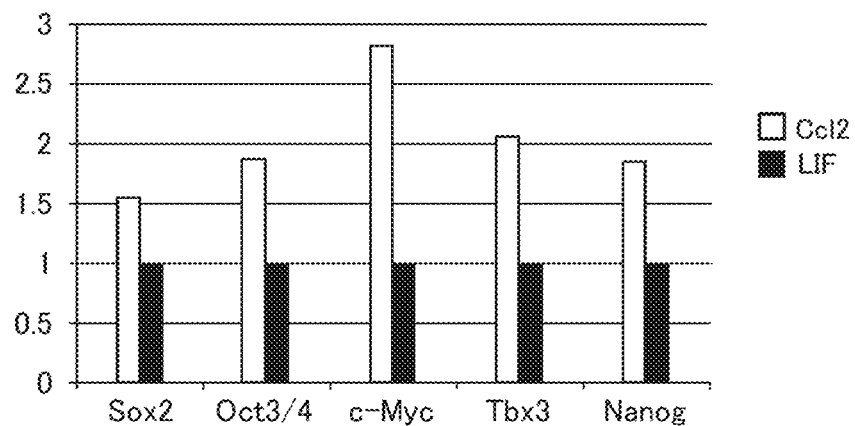
FIG. 13 is a graph showing the fold changes in expression of undifferentiated marker genes in mouse iPS cells cultured under the conditions where CCL2 was added and LIF was not added in still another example of the present invention.

The results are shown in FIG. 13. FIG. 13 is a graph showing the fold changes in expression of the undifferentiated marker genes in the mouse iPS cells cultured under the conditions where CCL2 was added and LIF was not added. The vertical axis indicates the fold change (-fold), and the horizontal axis indicates the results obtained in the example (open bars) and the results obtained in the comparative example (solid bars).

As can be seen from FIG. 13, even in the absence of LIF, which has been considered to be an essential component in culture under feeder free conditions, the expression of each undifferentiated marker gene increased markedly by the addition of the CCL2. From this result, it can be said that, for example, CCL2 can be used as a differentiation inhibitor either in combination with LIF or alone.

Example 7

In the present example, the human iPS cells were cultured in the presence of CCL2 under feeder conditions, and the effect of the CCL2 on the expression of the undifferentiated marker genes was examined.

The human iPS cells were used as undifferentiated cells, and human recombinant CCL2 (137-13011, WAKO, SEQ ID NO: 1) was used as the CCL2. The medium used was a medium for human stem cells (trade name "Primate ES medium", ReproCELL Incorporated). To this medium, LIF was not added, and the CCL2 was added. The concentration of the CCL2 in the medium was set to 500 ng/ml. Under the above-described feeder conditions, the human iPS cells were cultured on the feeder cells SNL76/7 that produce LIF in the above-described medium. Then, 6 days after the start of the culture, the feeder cells were removed, and total RNAs were collected from the cultured human iPS cells. The undifferentiated marker genes were then subjected to the quantitative RT-PCR.

Also, as a negative control, the human iPS cells were cultured under the feeder conditions and the undifferentiated marker genes were subjected to quantitative RT-PCR in the same manner as in the above, except that bFGF (derived from human, WAKO) was added instead of the CCL2 so that the concentration thereof was 5 ng/ml. Thereafter, assuming that the expression level in the comparative example was 1, the relative value with respect to this value was calculated as the fold change in expression level.

Figure 14:
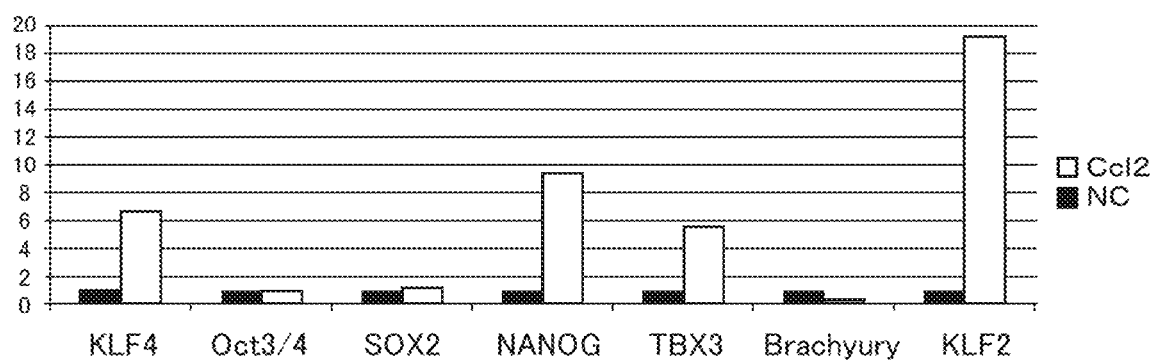
FIG. 14 is a graph showing the fold changes in expression of undifferentiated marker genes in human iPS cells in still another example of the present invention.

The results are shown in FIG. 14. FIG. 14 is a graph showing the fold changes in expression of the undifferentiated marker genes in the human iPS cells cultured in the presence of the CCL2. The vertical axis indicates the fold change (-fold), and the horizontal axis indicates the examined undifferentiated marker genes. The open bars show the results obtained in the example (CCL2), and the solid bars indicate the results obtained in the negative control (NC).

As can be seen from FIG. 14, when the human iPS cells were cultured in the presence of the human recombinant CCL2, the expressions of the undifferentiated marker genes, namely, the Nanog gene, the KLF4 gene, the STELLA gene, and the REX1 gene, increased markedly (about two-fold). These undifferentiated marker genes are marker genes indicating the blastocyst state (naive pluripotent state). Thus, it can be said that the human iPS cells were de-differentiated from the epiblast state to the blastocyst state.

Example 8

In the present example, regarding human iPS cells, the mechanism by which CCL2 promotes the Klf4 gene expression was analyzed.

(1) Effect of CCL2 on Phosphorylation in JaK/Stat3 Pathway

The promotion of phosphorylation of STAT3 in the Jak/Stat3 pathway by CCL2 was examined.

The human iPS cells were cultured under feeder conditions in the same manner as in Example 8, and the feeder cells were removed 6 days after the start of the culture. Then, in the same manner as in Example 3, the cultured human iPS cells were washed, suspended, homogenized, and centrifuged to collect the supernatant as a cell extract. Thereafter, a target protein was detected by Western blotting in the same manner as in Example 3, except that the above supernatant was used. Furthermore, as a negative control, the target protein was detected by carrying out the same procedures except that bFGF was added instead of the CCL2.

Then, the ratio of the phosphorylated STAT3 to the non-phosphorylated STAT3 (pSTAT3/STAT3) was determined. Assuming that the value of pSTAT3/STAT3 in the negative control was "1", the relative value was calculated.

The results are shown in FIG. 15. The photographs of FIG. 15A show the results of the Western blotting. In FIG. 15A, "NC" indicates the results obtained regarding the negative control, and "CCL2" indicates the results obtained when the mouse recombinant CCL2 was added. FIG. 15B is a graph showing the relative value of the ratio of the phosphorylated STAT3 to the non-phosphorylated STAT3 (pSTAT3/STAT3).

As can be seen from FIGS. 15A and 15B, by the addition of the CCL2, the ratio of the phosphorylated pSTAT3 to the non-phosphorylated STAT3 protein was increased to about 7.5-fold as compared to that in the negative control. That is, it was found that the phosphorylation of STAT3 was promoted by the presence of the CCL2. From these results, it is speculated that CCL2 promotes the expression of the Klf4 gene through phosphorylation of STAT3.

(2) Effect of CCL2 on Phosphorylation in PI3K Pathway

Regarding the activation of the PI3K pathway, phosphorylation of AKT serves as an indicator. Thus, promotion of the phosphorylation of AKT in the PI3K pathway was examined.

With respect to the supernatant prepared in the above item (1), the target protein detection was carried out in the same manner as in Example 4. Furthermore, as a negative control, the target protein detection was carried out in the same manner, except that bFGF was added instead of the CCL2.

Then, the ratio of the phosphorylated AKT to the non-phosphorylated AKT (p-AKT/AKT) was determined. Assuming that the value of the p-AKT/AKT in the negative control was "1", the relative value was calculated. Also, the ratio of the KLF4 gene expression to the GAPDH gene expression (KLF4/GAPDH) was determined. Assuming that KLF4/GAPDH in the negative control was "1", the relative value was calculated.

The results are shown in FIG. 15C. FIG. 15C is a graph showing the relative value regarding the ratio of the phosphorylated AKT to the non-phosphorylated AKT (pAKT/AKT). The results of the Western blotting also are shown in FIG. 15A. As can be seen from FIG. 15C, the phosphorylation of AKT was not promoted by the addition of the CCL2. It can be said that this suggests that the phosphorylation of AKT is not involved in the inhibition of the differentiation by CCL2.

Also, the ratio of KLF4 to GAPDH (KLF4/GAPDH) was determined. Assuming that KLF4/GAPDH in the negative control was "1", the relative value was calculated. The results are shown in FIG. 15D. FIG. 15D is a graph showing the relative value of the ratio of KLF4 to GAPDH (KLF4/GAPDH). The results of the Western blotting also are shown in FIG. 15A. As can be seen from FIG. 15D, as a result of comparison between the expression levels of KLF4 in the present example and the negative control after standardizing them with the expression levels of GAPDH, it was revealed that the KLF4 expression in the present example was about 1.7-fold higher than that in the negative control.

(3) Effect of Inhibition of Jak/Stat3 Pathway and PI3K Pathway

In the above item (1), it was suggested that the Jak/Stat3P pathway is involved in the improvement in the undifferentiation potency by CCL2, whereas the PI3K pathway is not involved therein. Thus, the effect of inhibition of these pathways on the undifferentiation potency by CCL2 was examined.

As a JAK inhibitor, a JAK inhibitor I (Merck) was used. As PI3K inhibitor, the same LY294002 as used in Example 4 was used. Human iPS cells were cultured for 6 days under feeder conditions in the same manner as in the above item (1), except that not only the CCL2 but also the JAK inhibitor or the PI3K inhibitor further was added to the medium. In the medium, the concentration of the Jak inhibitor was set to 10 ng/ml, and the concentration of the PI3K inhibitor was set to 5 ng/ml.

Furthermore, as a control, the cells were cultured in the same manner as in the above using the following media, respectively: a medium containing bFGF instead of the CCL2 and containing DMSO (5 ng/ml) instead of the inhibitor; and a medium containing bFGF (5 ng/ml) instead of the CCL2 and containing the inhibitor.

Figure 16:
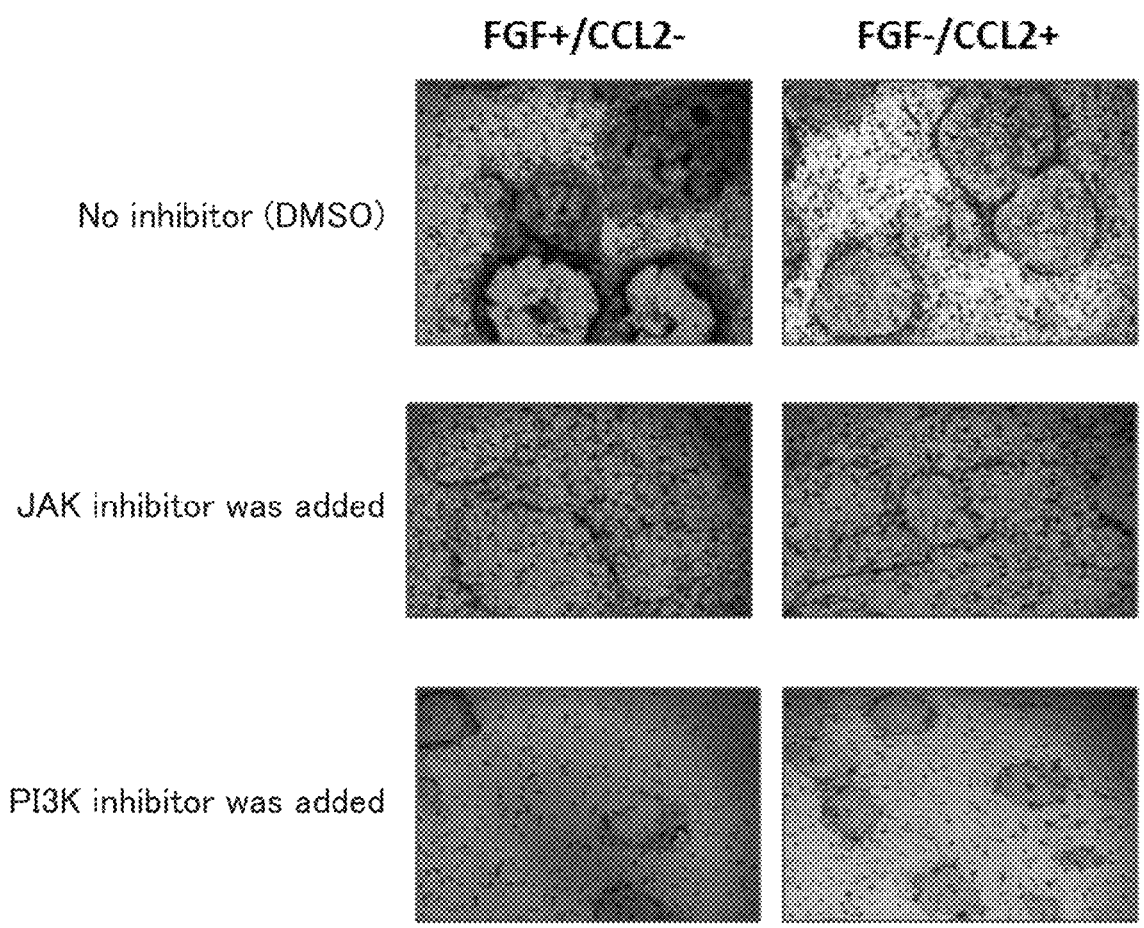
FIG. 16 shows photographs showing the morphology of human iPS cells cultured in the absence of feeder cells and in the presence of CCL2 in the example of the present invention.

The results are shown in FIG. 16. FIG. 16 shows phase-contrast micrographs of the human iPS cells after having been cultured for 6 days. In FIG. 16, the left lane shows the results obtained under the conditions of bFGF added (+)/CCL2 not added (−), and the right lane shows the results obtained under the conditions of bFGF not added (−)/CCL2 added (+). The phase-contrast micrographs show the results obtained under the conditions of, from the above: the inhibitor not added (DMSO added); the JAK inhibitor added; and the PI3K inhibitor added.

Under the conditions of the inhibitor not added (DMSO added)/bFGF(+)/CCL2(−), most of the cells maintained the undifferentiation potency, but some of the cells were differentiated. In contrast, under the conditions of the inhibitor not added (DMSO added)/bFGF(−)/CCL2(+), there were little differentiated cells unlike the former case. On the other hand, in the case where the Jak inhibitor was added, all the cells had been differentiated and many dead cells were observed under both the conditions of bFGF(+)/CCL2(−) and the conditions of bFGF(−)/CCL2(+). Furthermore, in the case where the PI3K inhibitor was added, almost all the cells had been differentiated and many dead cells were observed under the conditions of bFGF(+)/CCL2(−), whereas it was observed that many of the cells maintained the undifferentiation potency under the conditions of bFGF(−)/CCL2(+). These results also suggest that CCL2 maintains or improves the undifferentiation potency through the Jak/Stat3 pathway.

Example 9

In the present example, regarding human iPS cells, the effect of CCL2 on the cell adhesion and the growth potential was examined.

Figure 17:
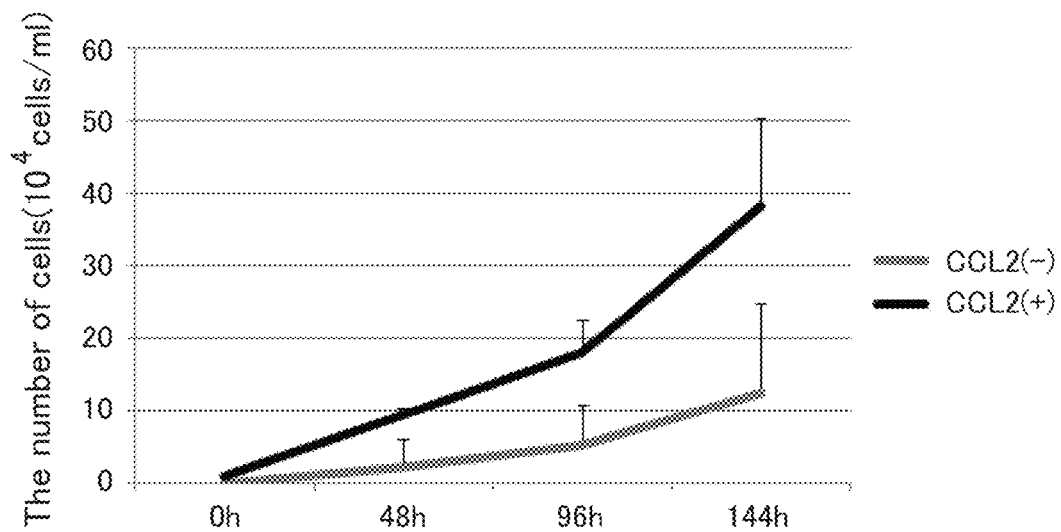
FIG. 17 is a graph showing the change with time in the number of human iPS cells cultured in the presence of CCL2 in still another example of the present invention.

Human iPS cells were cultured under feeder conditions in the same manner as in Example 8, and the number of cells was measured every 48 hours. As a negative control, the same procedures were carried out except that bFGF was added instead of the CCL2. The results are shown in FIG. 17. FIG. 17 is a graph showing the change with time in the number of the human iPS cells. The vertical axis indicates the number of cells ($10^4$ cells/ml), and the horizontal axis indicates the culture time (hr). CCL2(+) indicates the results obtained under the conditions of bFGF(−)/CCL2(+), and CCL2(−) indicates the results obtained under the conditions of bFGF(+)/CCL2(−).

As can be seen from FIG. 17, it was found that, when the CCL2 was added, the number of the cells was greater as of 48 hours than that when the CCL2 was not added because the number of the adherent cells was greater, and the growth potential was improved further as of 144 hours (on the 6th day). It is thus considered that the cell growth potential is improved if undifferentiated cells are in the blastocyst state (naive pluripotent state). Therefore, the results of the present example demonstrate that the human iPS cells in the undifferentiated state are de-differentiated from the epiblast state to the blastocyst state by CCL2.

Example 10

In the present example, the differentiation-inducing efficiency by CCL2 with respect to human iPS cells was examined.

(1) Observation of ES Cell-Like Morphology

Human iPS cells were cultured for 6 days under feeder conditions in the same manner as in Example 7. Thereafter, embryonic bodies (EBs) were produced. EB formation is known as a spontaneous differentiation-inducing method for inducing the differentiation of iPS cells. Specifically, first, a ROCK inhibitor (Y-27632, WAKO) was added to the culture solution being used for the culture of the human iPS cells so that the concentration thereof was 10 μl/ml, and the human iPS cells were cultured for 1 hour under the conditions of 37°

C. and 5% $CO_2$. Then, the feeder cells used for the culture were dissociated with a human ES/iPS cell dissociation solution (CTK solution), and the human iPS cells were collected. Then, $1\times10^6$ of the human iPS cells were seeded in an ultralow adhesion culture vessel, and cultured for 6 days in an EB preparation medium (DMEM/F12, Knockout SR, L-glutamine, NEAA (non-essential amino acid (GIBCO)), 2-ME, Pen/Strep). The medium was replaced every two days.

Figure 18A:
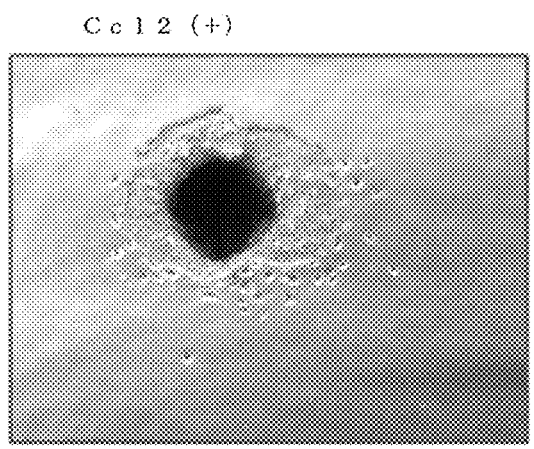
FIG. 18A shows the result of inducing spontaneous differentiation of an EB obtained from the human iPS cells cultured in the presence of CCL2.
Figure 18B:
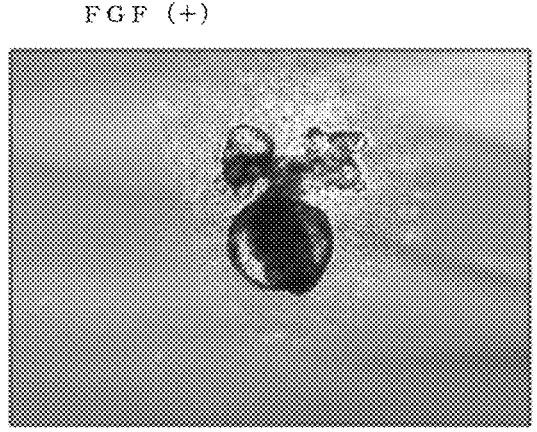
FIG. 18B shows the result of inducing spontaneous differentiation of an EB obtained from the human iPS cells cultured in the absence of CCL2.

Next, spontaneous differentiation was induced. Specifically, the produced EBs were seeded in gelatin coated dishes so that each gelatin coated dish contained one EB. Each EB was cultured for 14 days in a medium (DMEM) containing 20% FBS, and then observed with a microscope. The medium was replaced every two days. The results are shown in FIG. 18. The photographs in FIG. 18 show the cell morphology on the third day from the plating. FIG. 18A shows the result obtained when the mouse recombinant CCL2 was added, and FIG. 18B shows the result obtained when the bFGF was added.

As can be seen from FIG. 18, on the third day from the plating, the EB produced from the human iPS cells cultured in the presence of the CCL2 exhibited an ES cell-like morphology. In contrast, in the EB produced from the human iPS cells cultured in the presence of the bFGF, differentiation already had proceeded on the third day, and the EB exhibited an epithelial cell-like morphology.

(2) Checking of Differentiation to Myocardial Cells

It has been reported that, in general, according to the spontaneous differentiation-inducing method used in the above item (1), differentiation into myocardial cells is more liable to occur. Thus, regarding the cells on the 10th day from the plating in the above item (1), differentiation into myocardial cells was examined.

The morphology of the cells was examined with a microscope. Furthermore, they were immunostained with a Tropomyosin, which is a marker for myocardial cells. Also, culture of the cells, observation of the morphology, and staining were carried out in the same manner as in the above using a medium to which bFGF (5 ng/ml) has been added instead of the CCL2 and LIF.

Figure 19A:
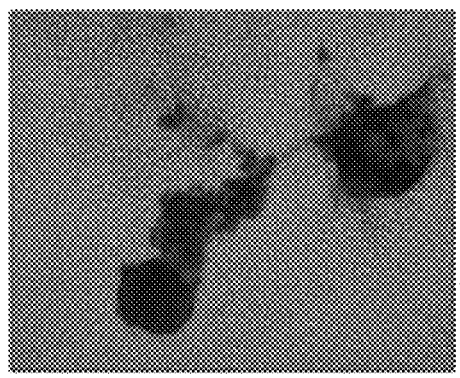
FIG. 19A shows the results obtained regarding EBs obtained from human iPS cell cultured in the absence of CCL2.
Figure 19B:
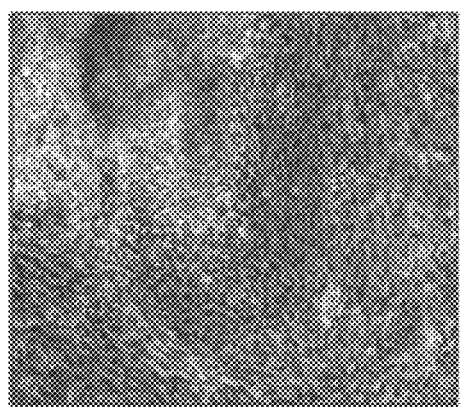
FIG. 19B shows the results obtained regarding EBs obtained from human iPS cells cultured in the presence of CCL2.

The results are shown in FIG. 19. The photographs in FIG. 19 show the morphologies of the cells on the 10th day from the plating of EB. FIG. 19A shows the results obtained under the conditions of CCL2 not added (−)/bFGF added (+), and FIG. 19B shows the results obtained under the conditions of CCL2 added (+)/LIF added (+). Furthermore, in FIGS. 19A and 19B, the photographs on the left show the cell morphologies, and the photographs on the right show the stained cells. In the black and white photographs of FIG. 19, the stained portions are seen as light gray.

As can be seen from FIG. 19A, regarding the EBs produced from the human iPS cells cultured under the conditions of the CCL2 not added and the bFGF added, it was found that, while some of them exhibited myocardial cell-like morphology, most of them were epithelial cell-like cells, which were not stained with the Tropomyosin. In contrast, as can be seen from FIG. 19B, regarding the EBs produced from the human iPS cells cultured in the presence of both the CCL2 and LIF, it was found that most of them exhibited myocardial cell-like morphology after the culture for 10 days, and they were entirely stained red with the Tripomyosin. From this result, it can be said that, the CCL2 caused the EBs to be more liable to differentiate into myocardial cells.

Example 11

In the present example, it was examined whether or not human iPS cells can be cultured in a feeder-free medium in the presence of LIF. Specifically, since it was confirmed in Example 9 that CCL2 improved the undifferentiation potency of the human iPS cells via Jak/Stat3, it was examined whether or not the human iPS cells can be cultured without feeder cells by allowing CCL2 to be present together with LIF.

As undifferentiated cells, the same human iPS cells as used in Example 7 were used. As CCL2, the mouse recombinant CCL2 used in the item (1) of Example 2 was used. As feeder free media, the following three kinds of media were provided by adding or not adding the CCL2, LIF and bFGF to the medium for human stem cells used in Example 8. Specifically, the media used were as follows: the medium with CCL2 not added (−)/LIF not added (−)/bFGF added (+); the medium with CCL2 added (+)/LIF not added (−)/bFGF not added (−); and the medium with CCL2 added (+)/LIF added (+)/bFGF not added (−). In each medium, the concentration of the LIF was set to 50 units/ml, the concentration of the CCL2 was set to 500 ng/ml, and the concentration of the bFGF was set to 5 ng/ml. Then, the human iPS cells were cultured for 6 days using each medium, and EBs were produced. Thereafter, the thus-produced EBs were seeded in gelatin coated dishes so that each gelatin coated dish contained one EB, and cultured for 5 days in a medium (DMEM) containing 20% FBS. Then, the cells after the culture were observed with a microscope.

Figure 20A:
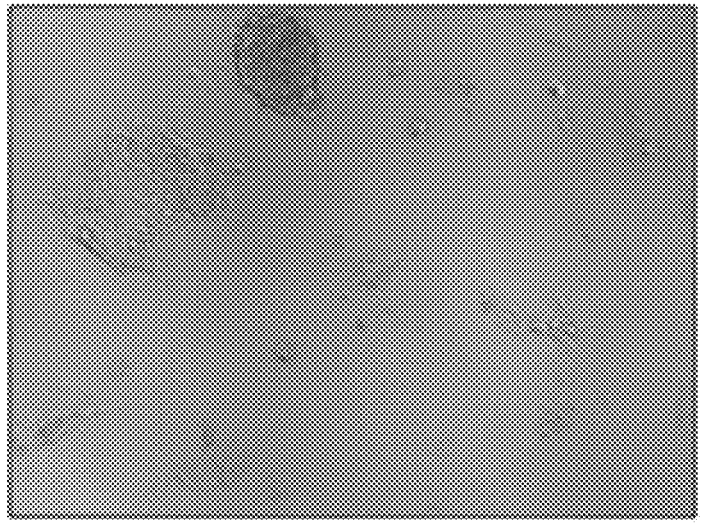
FIG. 20A shows the result obtained under the conditions of CCL2 added/LIF not added/bFGF not added.
Figure 20B:
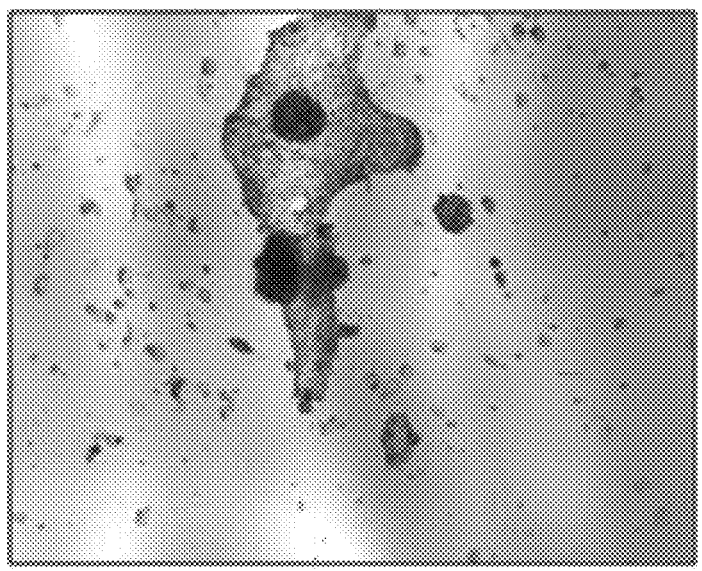
FIG. 20B shows the result obtained under the conditions of CCL2 added/LIF added/bFGF not added.

These results are shown in FIG. 20. The photographs in FIG. 20 show the cell morphologies of the EBs on the 5th day from the plating. FIG. 20A shows the result obtained under the conditions of the CCL2 added (+)/LIF not added (−)/bFGF not added (−). FIG. 20B shows the result obtained under the conditions of CCL2 added (+)/LIF added (+)/bFGF not added (−).

Under the conditions of CCL2 not added (−)/LIF not added (−)/bFGF added (+), cell adhesion was not observed (not shown in FIG. 20). In contrast, under the conditions of CCL2 added (+)/LIF added (+)/bFGF not added (−) (FIG. 20B), cell adhesion was observed, and also, by the culture for 5 days, colony growth was observed as shown in FIG. 20B. Furthermore, under the conditions of CCL2 added (+)/LIF not added (−)/bFGF not added (−), cell adhesion also was observed (FIG. 20A).

Example 12

Adherent cells exhibit different cell morphology than human iPS cells. Thus, in the present example, it was examined whether cells maintaining the undifferentiation potency actually are grown from the human iPS cells.

Specifically, human iPS cells were cultured under feeder conditions where bFGF was added and the CCL2 was not added, and under feeder free conditions where bFGF was not added and the CCL2 and LIF were added. Total RNAs then were extracted, and the expressions of undifferentiated marker genes were examined by the qRT-PCR. The culture under the feeder conditions was carried out in the same manner as in Example 8. The culture under the feeder free conditions was carried out in the same manner as in Example 12. Then, assuming that the expression level under the feeder condition was 1, the relative value with respect to this value was calculated as the fold change in expression level under the feeder free conditions.

Figure 21:
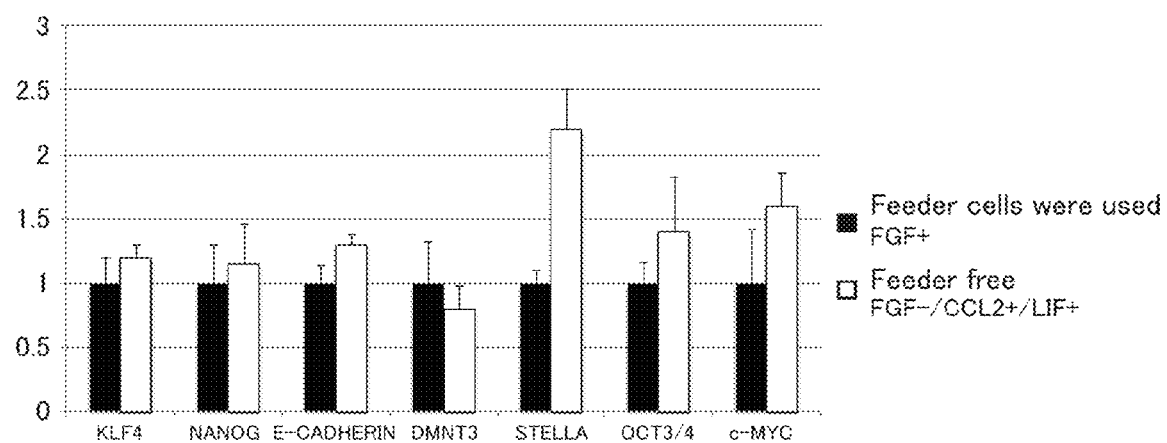
FIG. 21 is a graph showing the fold changes in expression of undifferentiated marker genes in human iPS cells cultured under feeder free conditions in still another example of the present invention.

The results are shown in FIG. 21. FIG. 21 is a graph showing the fold changes in the expression of the undifferentiated marker genes in the human iPS cells. The vertical axis indicates the fold change (-fold), and the horizontal axis indicates the examined undifferentiated marker genes. The open bars show the results obtained under the feeder free conditions, and the solid bars show the results obtained under the feeder conditions. As a result, the expressions of the undifferentiated marker genes under the feeder free conditions were comparable to those under the feeder conditions.

While the present invention has been described with reference to illustrative embodiments, the present invention is by no means limited to these embodiments. It is to be understood that changes and modifications that may become apparent to those skilled in the art may be made in the configuration and specifics of the present invention without departing from the scope of the present invention.

This application claims priority from Japanese Patent Application No. 2011-077473 filed on Mar. 31, 2011, and the entire disclosure thereof is incorporated herein by reference.

Also, the entire disclosures of all the patents, patent applications, and publication cited in the specification are incorporated herein by reference.

Industrial Applicability

As specifically described above, according to the present invention, by CCL2 or a protein containing a functional domain of the CCL2, an undifferentiated state of undifferentiated cells can be maintained and/or improved. According to the present invention, it is possible to culture undifferentiated cells such as ES cells and iPS cells with their undifferentiated state being maintained and/or improved, for example. Thus, the present invention is particularly useful for various medical applications including regenerative medicine and research thereon.

The invention claimed is:

1. A method for producing an undifferentiated cell with an undifferentiated state of the undifferentiated cell being controlled, the method comprising:
   culturing the undifferentiated cell in the absence of basic fibroblast growth factor (bFGF) and in the presence C-C motif chemokine 2 (CCL2) or a protein comprising a functional domain of the CCL2, wherein the functional domain of the CCL2 is a portion of the CCL2, which corresponds to the region consisting of the amino acid seguence of SEQ ID NO: 2 in human CCL2 or the region consisting of the amino acid sequence of SEQ ID NO: 4 in mouse CCL2.

2. A method for controlling an undifferentiated state of an undifferentiated cell, the method comprising:
   culturing the undifferentiated cell by the production method according to claim 1, thereby maintaining and/ or improving the undifferentiated state of the undifferentiated cell.

3. The method according to claim 1, wherein the undifferentiated cells are embryonic stem (ES) cells or induced pluripotent stem (iPS) cells.

4. A method for producing an undifferentiated cell with an undifferentiated state of the undifferentiated cell being controlled, the method comprising:
   culturing the undifferentiated cell in the absence of basic fibroblast growth factor (bFGF) and in the presence of C-C motif chemokine 2 (CCL2) or a protein comprising a functional domain of the CCL2, wherein the functional domain of the CCL2 is a portion of the CCL2, which corresponds to the region consisting of the amino acid sequence of SEQ ID NO: 2 in human CCL2 or the region consisting of the amino acid sequence of SEQ ID NO: 4 in mouse CCL2, and wherein the CCL2 or the functional domain of the CCL2 is expressed from an expression vector that is introduced into a host cell and expresses the CCL2 or the functional domain of the CCL2.

5. The method according to claim 4, wherein the undifferentiated cells are embryonic stem (ES) cells or induced pluripotent stem (iPS) cells.

\* \* \* \* \*